US009474552B2

(12) United States Patent
Barnett et al.

(10) Patent No.: US 9,474,552 B2
(45) Date of Patent: Oct. 25, 2016

(54) RATCHETING STRUT

(75) Inventors: Gary D. Barnett, Wabash, IN (US);
Paul Slagle, Fort Wayne, IN (US);
Mark Lester, Warsaw, IN (US); Mark R. Brinker, Houston, TX (US); Philip H. Frank, Maplewood, NJ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 692 days.

(21) Appl. No.: 13/464,502

(22) Filed: May 4, 2012

(65) Prior Publication Data
US 2013/0296857 A1 Nov. 7, 2013

(51) Int. Cl.
A61B 17/64 (2006.01)
A61B 17/66 (2006.01)
A61B 17/70 (2006.01)

(52) U.S. Cl.
CPC .......... *A61B 17/6416* (2013.01); *A61B 17/64* (2013.01); *A61B 17/66* (2013.01); *A61B 17/7014* (2013.01)

(58) Field of Classification Search
CPC .. A61B 17/60; A61B 17/66; A61B 17/7014; A61B 2017/606
USPC ...................................... 606/53–59
See application file for complete search history.

(56) References Cited

U.S. PATENT DOCUMENTS

| 4,308,863 | A * | 1/1982 | Fischer ........................ 606/57 |
| 8,439,914 | B2 | 5/2013 | Ross et al. |
| 2006/0195087 | A1 * | 8/2006 | Sacher et al. .................. 606/61 |
| 2006/0217735 | A1 * | 9/2006 | MacDonald et al. ........... 606/90 |
| 2009/0216231 | A1 * | 8/2009 | Lanz .............................. 606/59 |
| 2011/0137347 | A1 * | 6/2011 | Hunziker .......... A61B 17/7016 606/258 |
| 2011/0208187 | A1 | 8/2011 | Wong |
| 2012/0203225 | A1 | 8/2012 | Mingozzi et al. |

FOREIGN PATENT DOCUMENTS

| WO | WO 00/53109 A1 | 9/2000 |
| WO | WO 2006/126167 A2 | 11/2006 |
| WO | WO 2009/102904 A1 | 8/2009 |

OTHER PUBLICATIONS

International Search Report and Written Opinion for PCT/US2013/031539 mailed Jun. 28, 2013.

* cited by examiner

*Primary Examiner* — Nicholas Plionis
(74) *Attorney, Agent, or Firm* — Schwegman Lundberg & Woessner, P.A.

(57) ABSTRACT

A ratcheting strut comprising: (a) a ratchet box including a through passage; (b) a first tube sized to extend at least partially through the passage, the first tube including ratchet teeth that engage corresponding ratchet teeth of the ratchet box; (c) a second tube mounted to the ratchet box in parallel with the first tube, the second tube operatively coupled to a second fixation adapter; and (d) a threaded rod operatively coupled to a nut and a first fixation adapter, the threaded rod repositionably mounted to the first tube, where the nut is operatively coupled and repositionable with respect to the first tube.

7 Claims, 34 Drawing Sheets

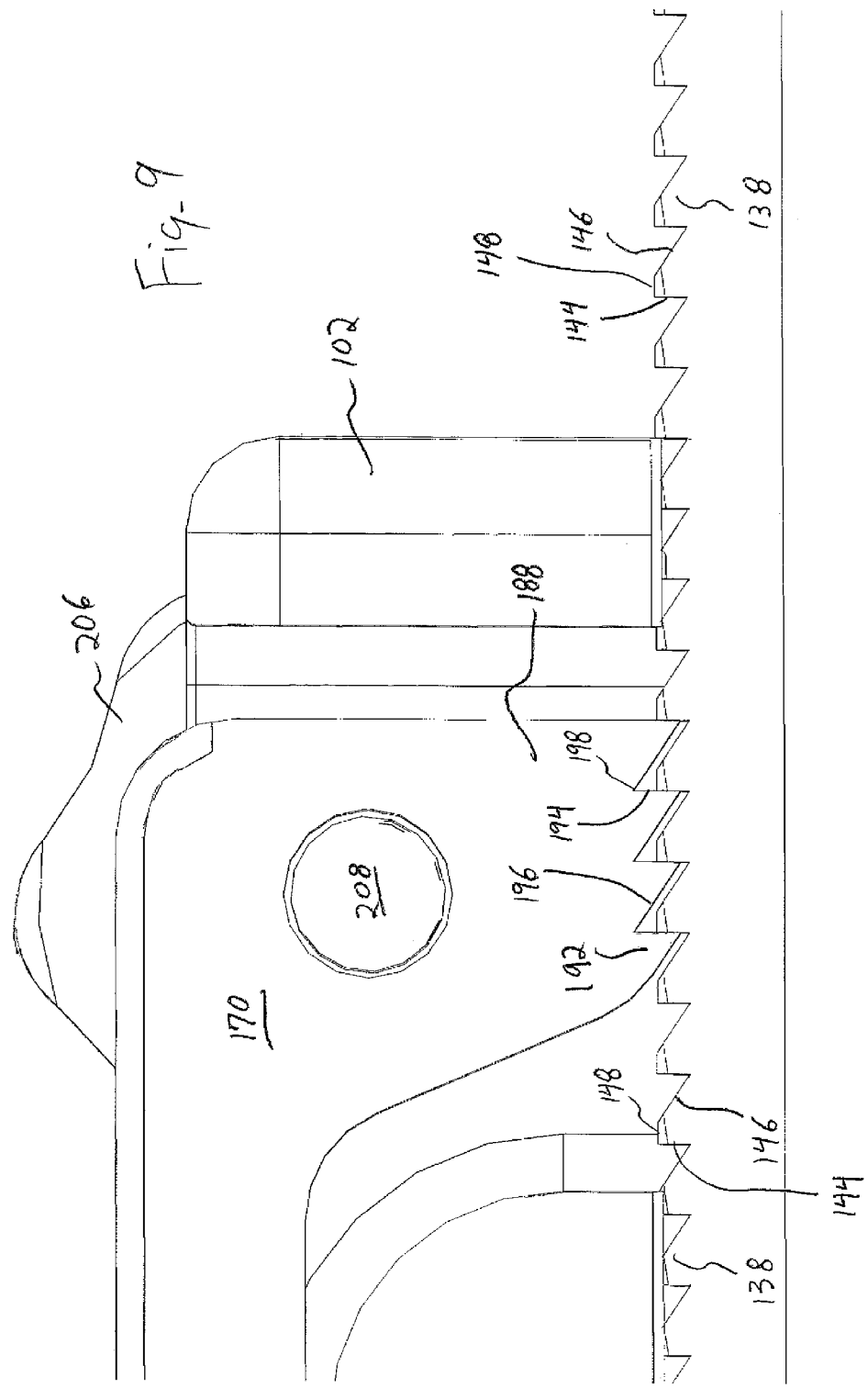

RATCHETING STRUT

RELATED ART

Field of the Invention

The present invention is directed to devices and methods utilized in fracture reduction and, more specifically, to devices and methods providing length adjustment during fracture fixation.

INTRODUCTION TO THE INVENTION

The present invention is directed to devices and methods utilized in fracture reduction and, more specifically, to devices and methods providing length adjustment during fracture fixation. The present invention may include modular (re)movable struts that can be interchanged depending upon the distance to be spanned (i.e., span fracture in a single long bone, or cross the knee joint). In one exemplary embodiment, a ratcheting strut is disclosed that provides for length adjustment during fracture fixation and reduction.

It is a first aspect of the present invention to provide a ratcheting strut comprising: (a) a ratchet box including a through passage; (b) a first tube sized to extend at least partially through the passage, the first tube including ratchet teeth that engage corresponding ratchet teeth of the ratchet box; (c) a second tube mounted to the ratchet box in parallel with the first tube, the second tube operatively coupled to a second fixation adapter; and, (d) a threaded rod operatively coupled to a nut and a first fixation adapter, the threaded rod repositionably mounted to the first tube, where the nut is operatively coupled and repositionable with respect to the first tube.

In a more detailed embodiment of the first aspect, the second tube is longitudinally axially offset from the first tube. In yet another more detailed embodiment, the second tube includes a fixed length and is removably coupled to the ratchet box. In a further detailed embodiment, the second tube is removably mounted to the ratchet box, and the second tube is removably mounted to the second fixation adapter. In still a further detailed embodiment, the fixation adapter includes at least one of a ball joint, a ball joint housing, and a ball joint cap. In a more detailed embodiment, the ratchet box includes a first lever repositionable between an engaged position and a disengaged position, the first lever includes the ratchet teeth of the ratchet box, the ratchet teeth of the lever engage the ratchet teeth of the first tube in the engaged position, and the ratchet teeth of the lever do not engage the ratchet teeth of the first tube in the disengaged position. In a more detailed embodiment, a plurality of the ratchet teeth of the first lever each include a profile including an inclined surface and a vertical surface, a plurality of the ratchet teeth of the first tube each include a profile including an inclined surface and a vertical surface, the inclined surfaces of the ratchet teeth of the first lever are substantially parallel to the inclined surfaces of the ratchet teeth of the first tube when in the engaged position, and the vertical surfaces of the ratchet teeth of the first lever are substantially parallel to the vertical surfaces of the ratchet teeth of the first tube when in the engaged position. In another more detailed embodiment, the lever is biased to the engaged position. In yet another more detailed embodiment, the ratchet box includes a first lever repositionable between an engaged position and a disengaged position, and a second lever repositionable between an engaged position and a disengaged position, the first lever includes a first portion of the ratchet teeth of the ratchet box, the second lever includes a second portion of the ratchet teeth of the ratchet box, the ratchet teeth of the ratchet tube include a first row and a second row, the first portion of the ratchet teeth of the first lever engage the first row of the ratchet teeth of the first tube in the engaged position, the second portion of the ratchet teeth of the second lever engage the second row of the ratchet teeth of the first tube in the engaged position, the first portion of the ratchet teeth of the first lever do not engage the first row of the ratchet teeth of the first tube in the disengaged position, and the second portion of the ratchet teeth of the second lever do not engage the second row of the ratchet teeth of the first tube in the disengaged position. In still another more detailed embodiment, a plurality of the first portion of the ratchet teeth each include a profile including an inclined surface and a vertical surface, a plurality of the second portion of the ratchet teeth each include a profile including an inclined surface and a vertical surface, a plurality of the first row of the ratchet teeth each include a profile including an inclined surface and a vertical surface, a plurality of the second row of the ratchet teeth each include a profile including an inclined surface and a vertical surface, the inclined surfaces of first and second rows are parallel to one another, and the inclined surfaces of the first and second portions are parallel to one another when the first and second levers are both in the engaged position.

In yet another more detailed embodiment of the first aspect, the ratchet box includes a first lever repositionable between an engaged position and a disengaged position, and a second lever repositionable between an engaged position and a disengaged position, the first lever includes a first portion of the ratchet teeth of the ratchet box, the second lever includes a second portion of the ratchet teeth of the ratchet box, the ratchet teeth of the ratchet tube include a first row and a second row, an interaction between the first portion of the ratchet teeth and the first row of ratchet teeth prohibit movement between the ratchet box and the ratchet tube in a first direction when the first lever is in the engaged position, but allows movement between the ratchet box and the ratchet tube in a second direction, opposite the first direction, when the first lever is in the engaged position and the second lever is in the disengaged position, and an interaction between the second portion of the ratchet teeth and the second row of ratchet teeth prohibit movement between the ratchet box and the ratchet tube in the second direction when the second lever is in the engaged position, but allows movement between the ratchet box and the ratchet tube in the first direction when the second lever is in the engaged position and the first lever is in the disengaged position. In still another more detailed embodiment, the second tube is at least partially hollow and includes a cavity adapted to be partially occupied by the first tube, and the first tube is at least partially hollow and includes a cavity adapted to be partially occupied by the threaded rod. In a further detailed embodiment, the first tube, the second tube, and the threaded rod telescopically interact with one another. In still a further detailed embodiment, the threaded rod is removably mounted to the second fixation adapter, and the fixation adapter includes at least one of a ball joint, a ball joint housing, and a ball joint cap. In a more detailed embodiment, the threaded rod is operatively coupled to a friction sleeve that is received within the first tube. In a more detailed embodiment, the threaded rod is removably mounted to a post cap that is received within the first tube, and the friction sleeve is removably mounted to the post cap. In another more detailed embodiment, the first tube includes a tube mount coupled to an end thereof, the tube mount includes a through orifice and a circumferential channel that receives a projection from the nut so that the nut rotationally engages the tube mount, the threaded rod is sized to extend through the tube mount orifice, and threads of the threaded rod are sized to engage threads of the nut so that rotation of the nut results in longitudinal repositioning of the threaded rod.

It is a second aspect of the present invention to provide a bone fracture fixation device comprising: (a) a first tube being repositionable with respect to a second tube in predetermined longitudinal increments, wherein the first tube is associated with a first actuator biased to engage the second tube to retard motion of the first tube with respect to the second tube in a first direction, where the first tube and the second tube extend in opposite directions, and where at least one of the first tube and the second tube includes an extension operatively coupled thereto that is repositionable to increase an aggregate length of at least one of the first tube and the second tube, wherein the extension is repositionable in longitudinal increments smaller than the predetermined longitudinal increments.

In a more detailed embodiment of the second aspect, the longitudinal increments of the extension are infinitely small. In yet another more detailed embodiment, the second tube is longitudinally axially offset from the first tube. In a further detailed embodiment, the first tube and the second tube each include a fixed length, and where the first tube includes a hollow interior to accommodate at least a portion of the second tube. In still a further detailed embodiment, the second tube is removably mounted to the first tube, and the second tube is removably mounted to a fixation adapter. In a more detailed embodiment, the fixation adapter includes at least one of a ball joint, a ball joint housing, and a ball joint cap. In a more detailed embodiment, the actuator includes a first lever repositionable between an engaged position and a disengaged position, the first lever includes ratchet teeth, the ratchet teeth of the first lever engage ratchet teeth of the second tube in the engaged position, and the ratchet teeth of the first lever do not engage the ratchet teeth of the second tube in the disengaged position. In another more detailed embodiment, a plurality of the ratchet teeth of the first lever each include a profile including an inclined surface and a vertical surface, a plurality of the ratchet teeth of the second tube each include a profile including an inclined surface and a vertical surface, the inclined surfaces of the ratchet teeth of the first lever are substantially parallel to the inclined surfaces of the ratchet teeth of the second tube when in the engaged position, and the vertical surfaces of the ratchet teeth of the first lever are substantially parallel to the vertical surfaces of the ratchet teeth of the second tube when in the engaged position.

In yet another more detailed embodiment of the second aspect, the first tube is associated with a second actuator biased to engage the second tube to retard motion of the first tube with respect to the second tube in a second direction, opposite the first direction, the actuator is repositionable between an engaged position and a disengaged position, the second actuator is repositionable between an engaged position and a disengaged position, the second tube includes a first series of teeth and a second series of teeth, the first actuator engages the first series of teeth in the engaged position, the second actuator engages the second series of teeth in the engaged position, the first actuator does not engage the first series of teeth in the disengaged position, and the second actuator does not engage the second series of teeth in the disengaged position. In still another more detailed embodiment, a plurality of the first series of the teeth each include a profile including an inclined surface and a vertical surface, a plurality of the second series of the teeth each include a profile including an inclined surface and a vertical surface, the first actuator includes at least one tooth including a profile including an inclined surface and a vertical surface, the second actuator includes at least one tooth including a profile including an inclined surface and a vertical surface, the inclined surfaces of the first and second series of teeth are parallel to one another, and the inclined surfaces of the at least one tooth of the first and second actuators are parallel to one another when the first and second actuators are both in the engaged position. In a further detailed embodiment, the first tube is at least partially hollow and includes a cavity adapted to be partially occupied by the second tube, and the second tube is at least partially hollow and includes a cavity adapted to be partially occupied by the extension. In still a further detailed embodiment, the first tube, the second tube, and the extension telescopically interact with one another. In a more detailed embodiment, the extension is removably mounted to a first fixation adapter, and the first fixation adapter includes at least one of a ball joint, a ball joint housing, and a ball joint cap. In a more detailed embodiment, the extension is operatively coupled to a friction sleeve that is received within the second tube. In another more detailed embodiment, the extension is removably mounted to a post cap that is received within the first tube, and the friction sleeve is removably mounted to the post cap. In yet another more detailed embodiment, the second tube includes a tube mount coupled to an end thereof, the tube mount includes a through orifice and a circumferential channel that receives a projection from a nut so that the nut rotationally engages the tube mount, the extension is sized to extend through the tube mount orifice, and threads of the extension are sized to engage threads of the nut so that rotation of the nut results in longitudinal repositioning of the extension with respect to the first and second tubes.

It is a third aspect of the present invention to provide a method of using a fracture fixation device that includes opposing longitudinal tubes that are repositionable with respect to one another to increase and decrease a total distance between opposing ends of the longitudinal tubes, the method comprising: (a) repositioning a first of the longitudinal tubes with respect to a second of the longitudinal tubes in a first direction so that a first series of teeth associated with the first longitudinal tube slides upon a first series of teeth associated with the second longitudinal tube; and, (b) repositioning a first blocking actuator associated with at least one of the first and second longitudinal tubes to discontinue engagement of the first series of teeth of the first longitudinal tube with the first series of teeth of the second longitudinal tube in order to reposition the first longitudinal tube with respect to the second longitudinal tube in a second direction, opposite the first direction In a more detailed embodiment of the third aspect, the step of repositioning the first longitudinal tube with respect to the second longitudinal tube in the first direction includes repositioning a second blocking actuator associated with at least one of the first longitudinal tube and the second longitudinal tube to discontinue engagement of a second series of teeth of the first longitudinal tube with a second series of teeth of the second longitudinal tube. In yet another more detailed embodiment, the step of repositioning a first blocking actuator associated with at least one of the first and second longitudinal tubes includes repositioning a second blocking actuator associated with at least one of the first longitudinal tube and the second longitudinal tube to engage a second series of teeth of the first longitudinal tube with a second series of teeth of the second longitudinal tube. In a further detailed embodiment, the method further includes repositioning a first extension operatively coupled to at least one of the longitudinal tubes, where repositioning of the first longitudinal tube with respect to the second longitudinal tube is carried out in predetermined longitudinal increments defined by the dimensions of the first and second series of teeth, and repositioning of the first extension is carried out in longitudinal increments smaller than the predetermined longitudinal increments provided by the first and second series of teeth.

BRIEF DESCRIPTION OF THE DRAWINGS

FIG. 9 is a magnified view of the ratchet box and internal components shown in FIG. 8.

FIG. 10 is an elevated perspective view showing assembly of several of the components of FIG. 1.

DETAILED DESCRIPTION

Figure 1:
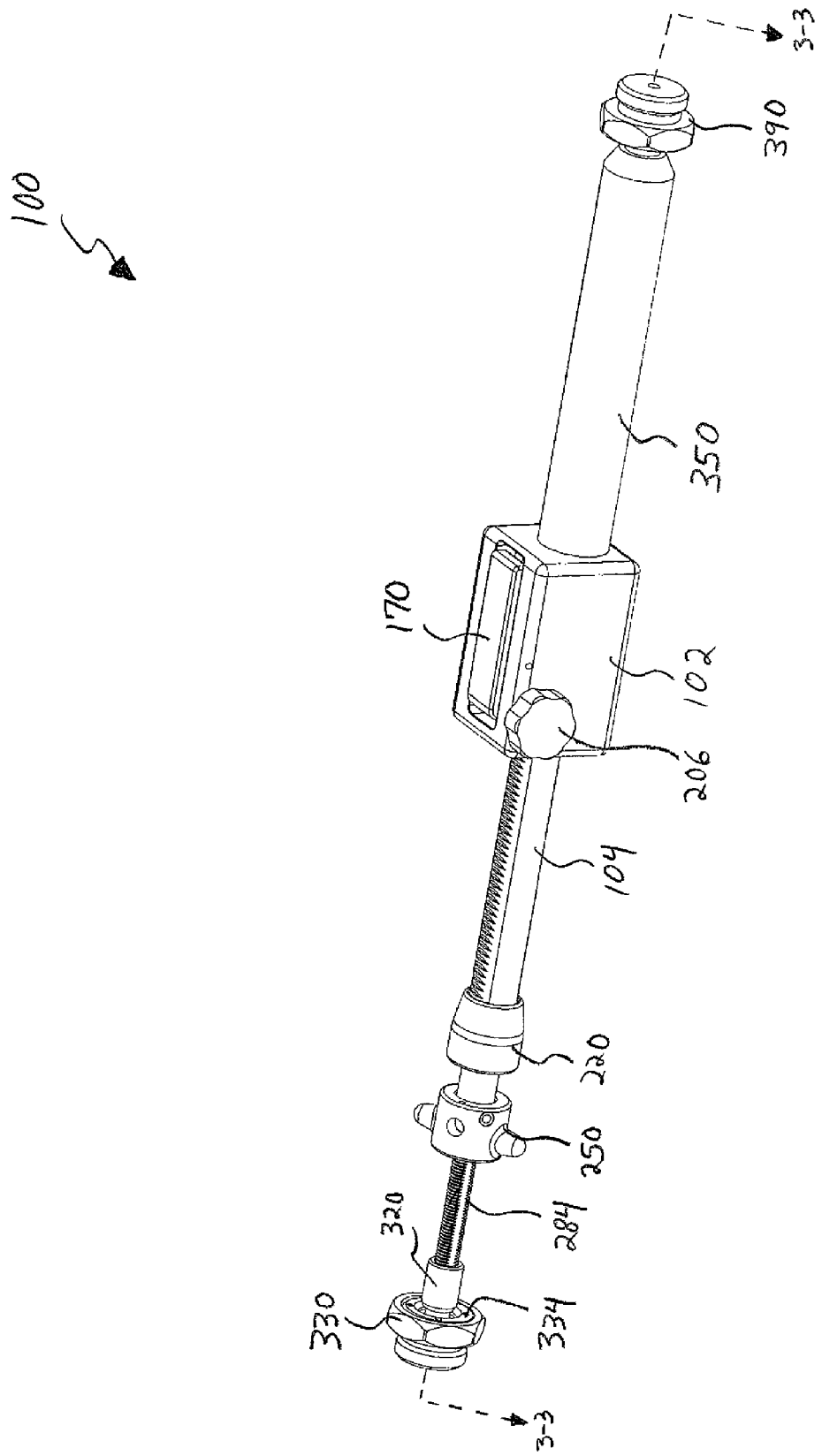
FIG. 1 is an elevated perspective view of an assembled first exemplary ratcheting strut in accordance with the instant disclosure.
Figure 2:
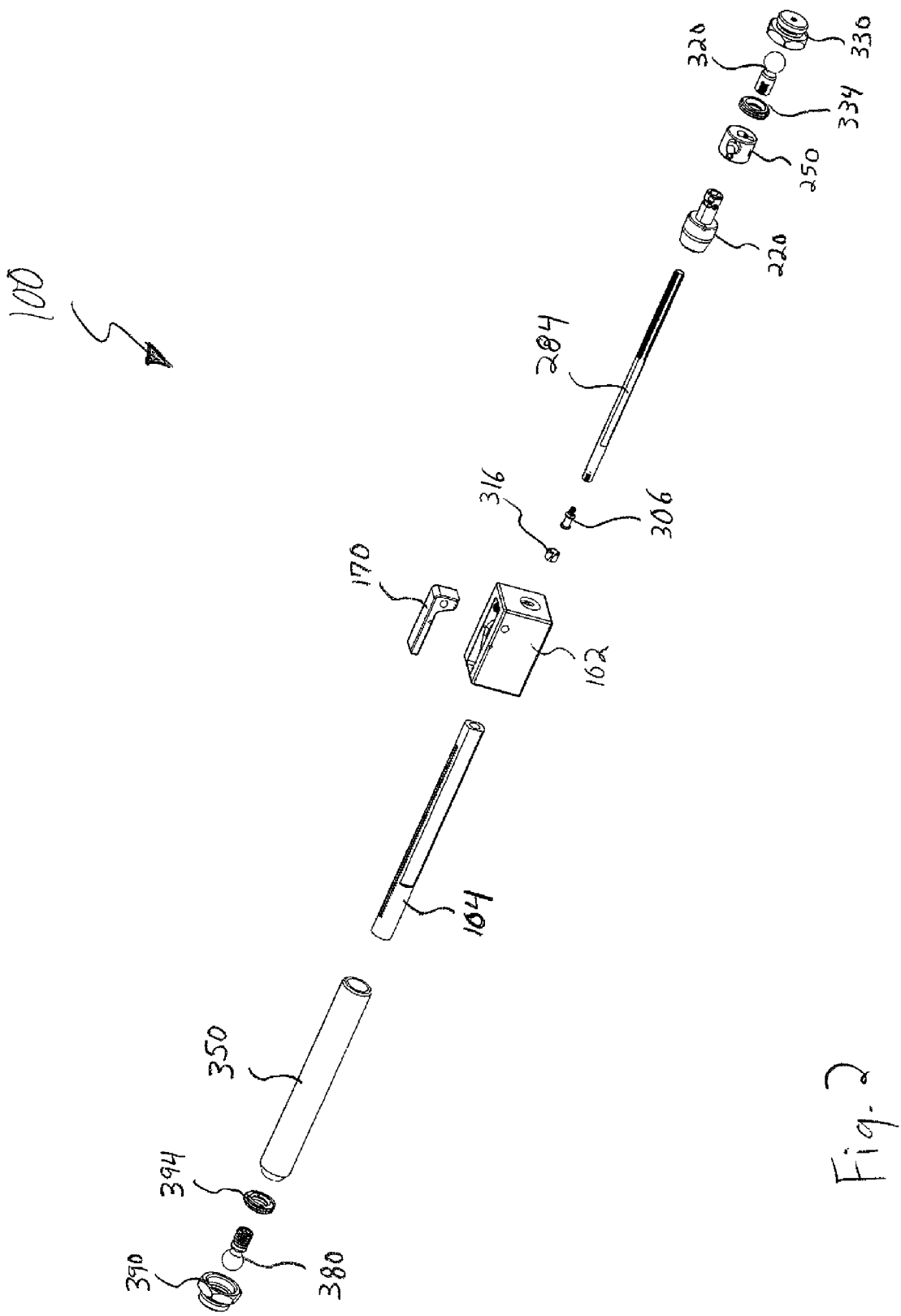
FIG. 2 is an exploded view of the first exemplary ratcheting strut of FIG. 1 without the thumb screw.
Figure 3:
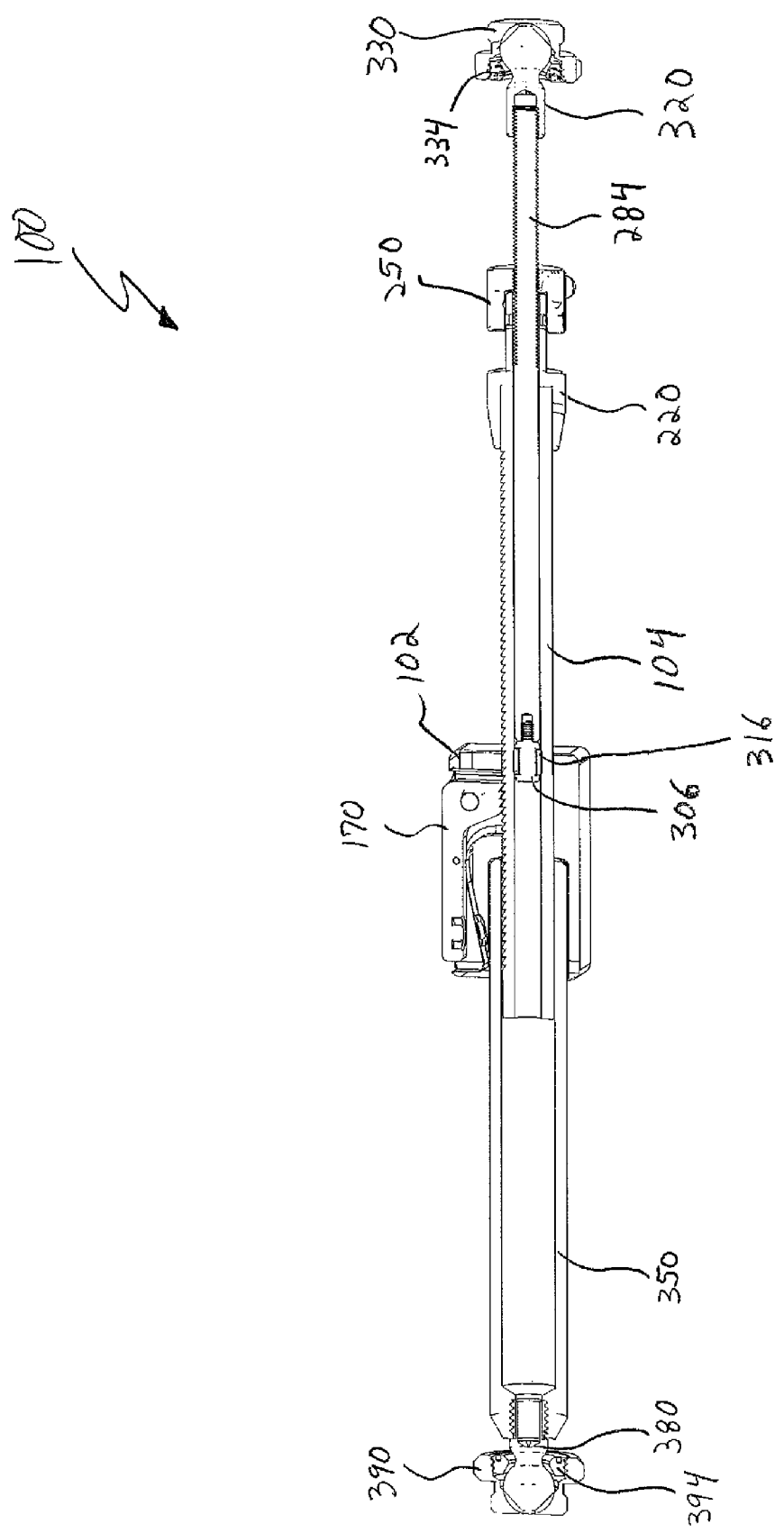
FIG. 3 is a cross-sectional view of the first exemplary ratcheting strut of FIG. 1 taken along line 3-3.
Figure 4:
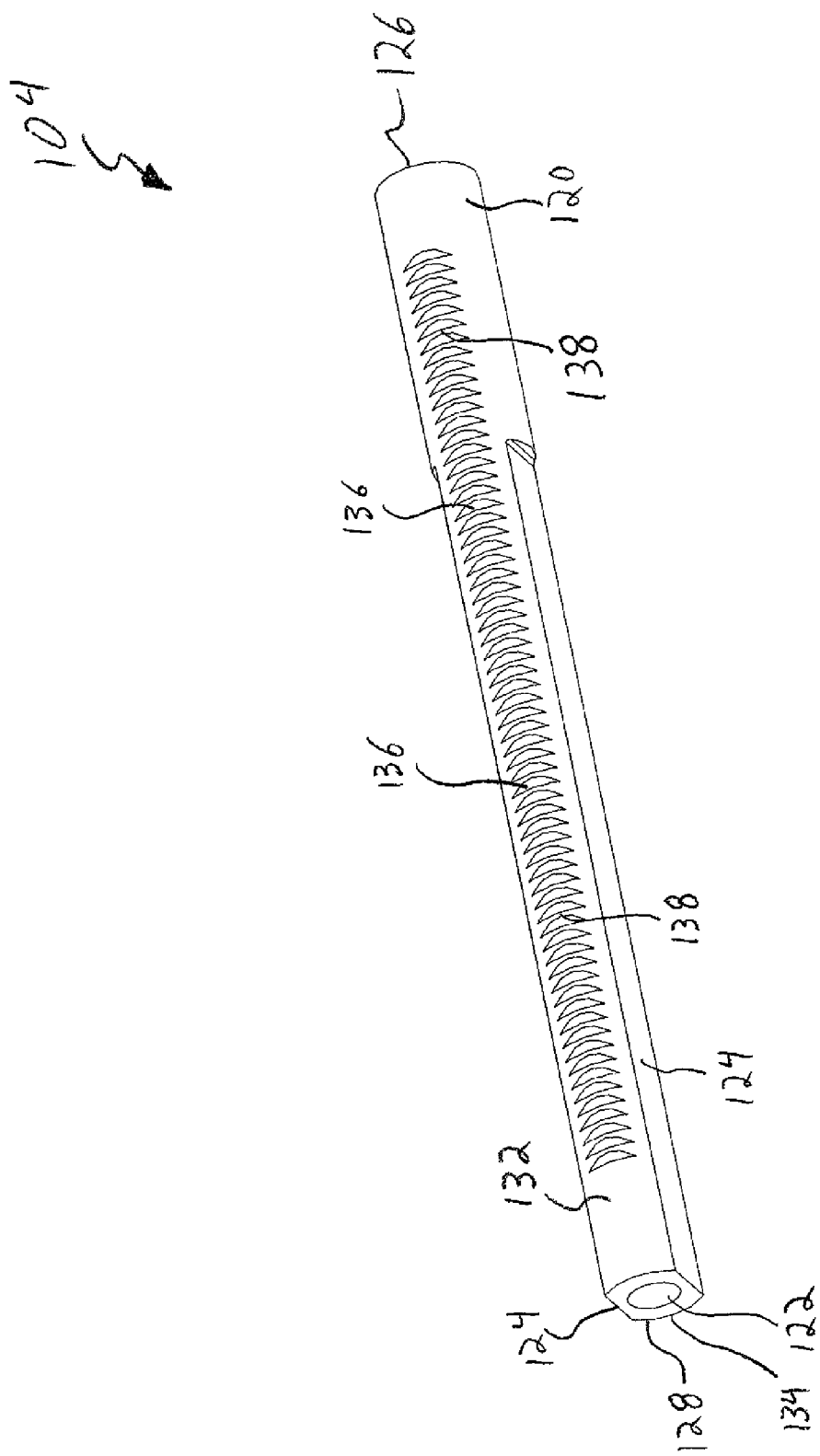
FIG. 4 is an elevated perspective view of the exemplary ratchet tube of FIG. 1.
Figure 5:
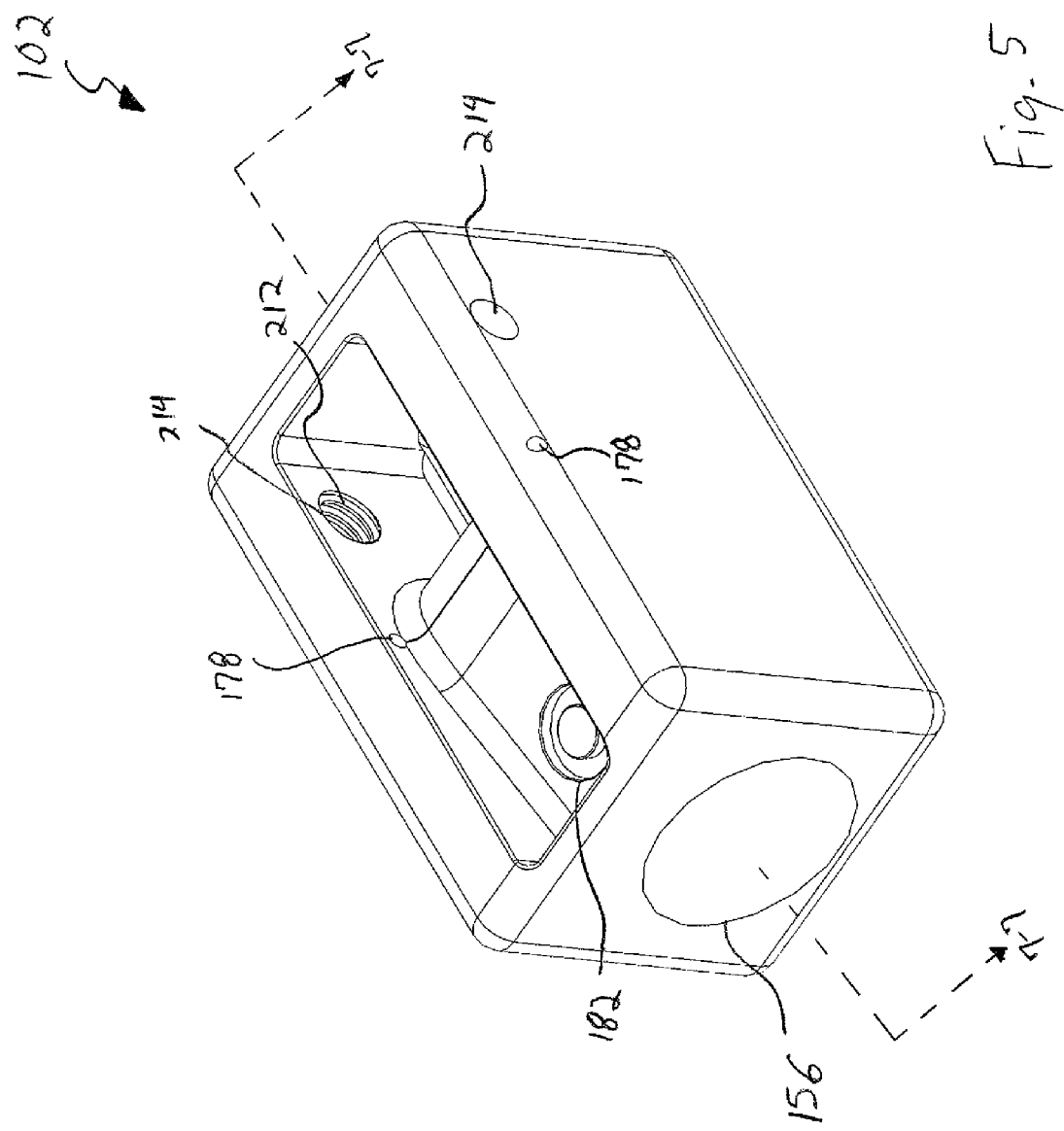
FIG. 5 is an elevated perspective view of the exemplary ratchet box of FIG. 1.
Figure 6:
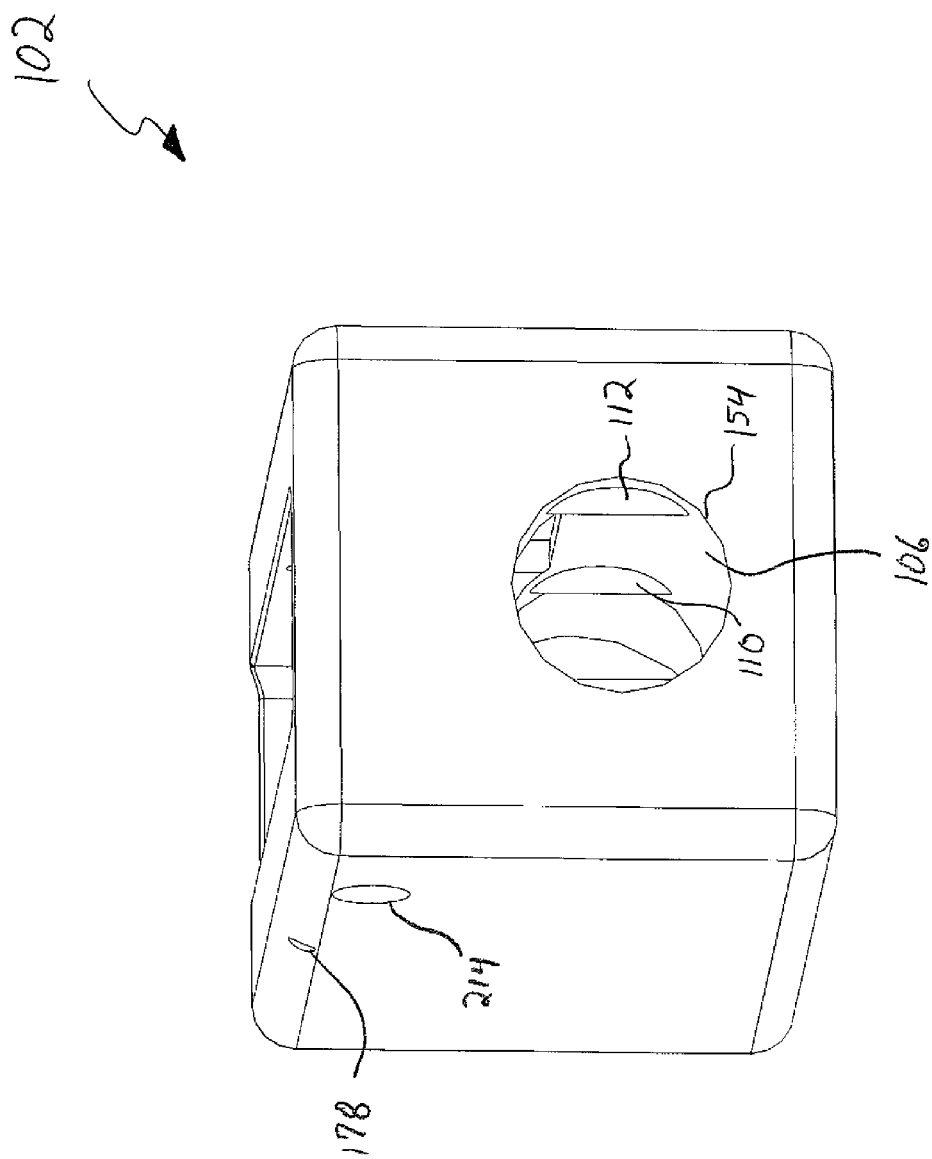
FIG. 6 is another elevated perspective view of the exemplary ratchet box of FIG.
Figure 7:
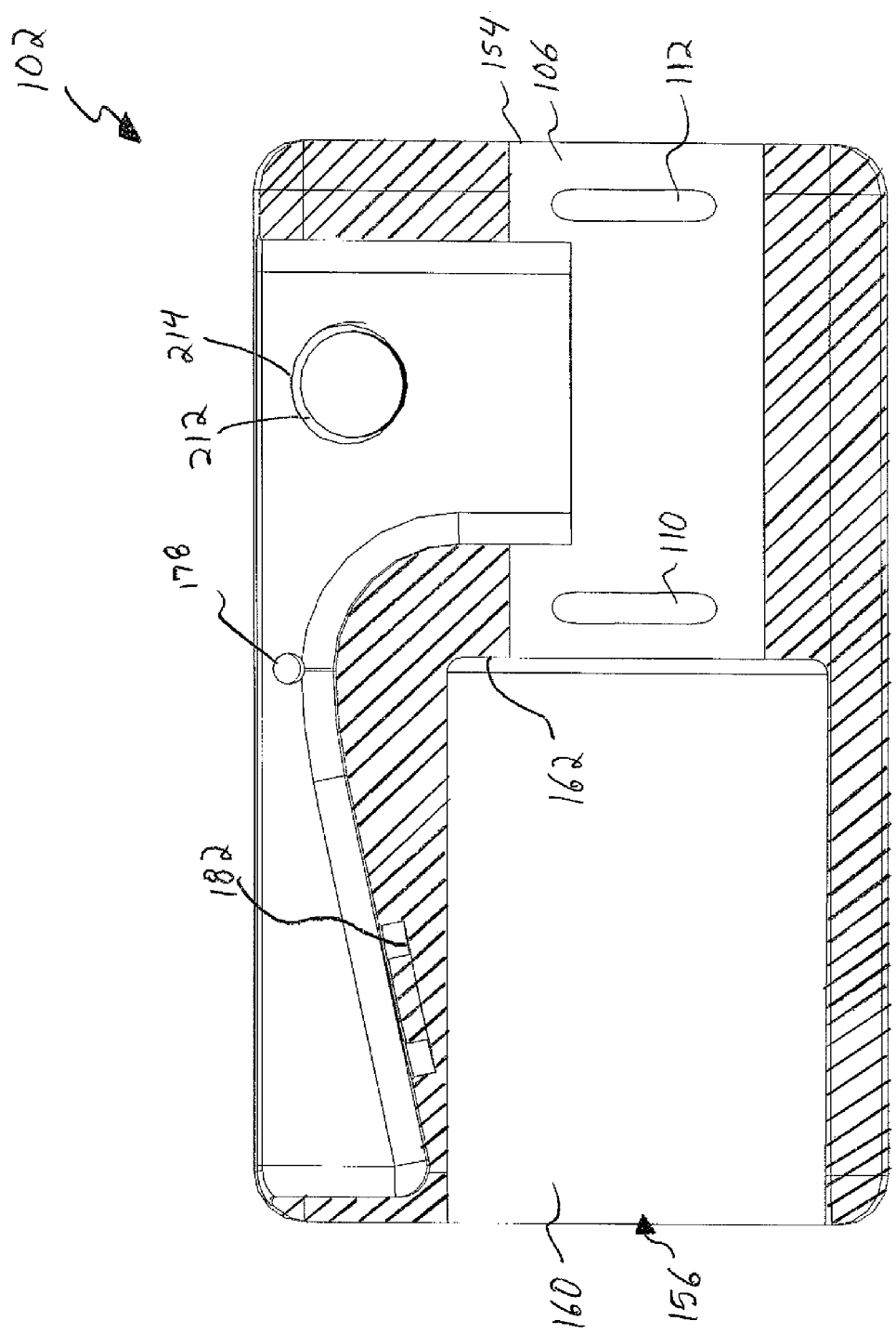
FIG. 7 is a cross-sectional view of the first exemplary ratcheting box of FIG. 5 taken along line 7-7.
Figure 8:
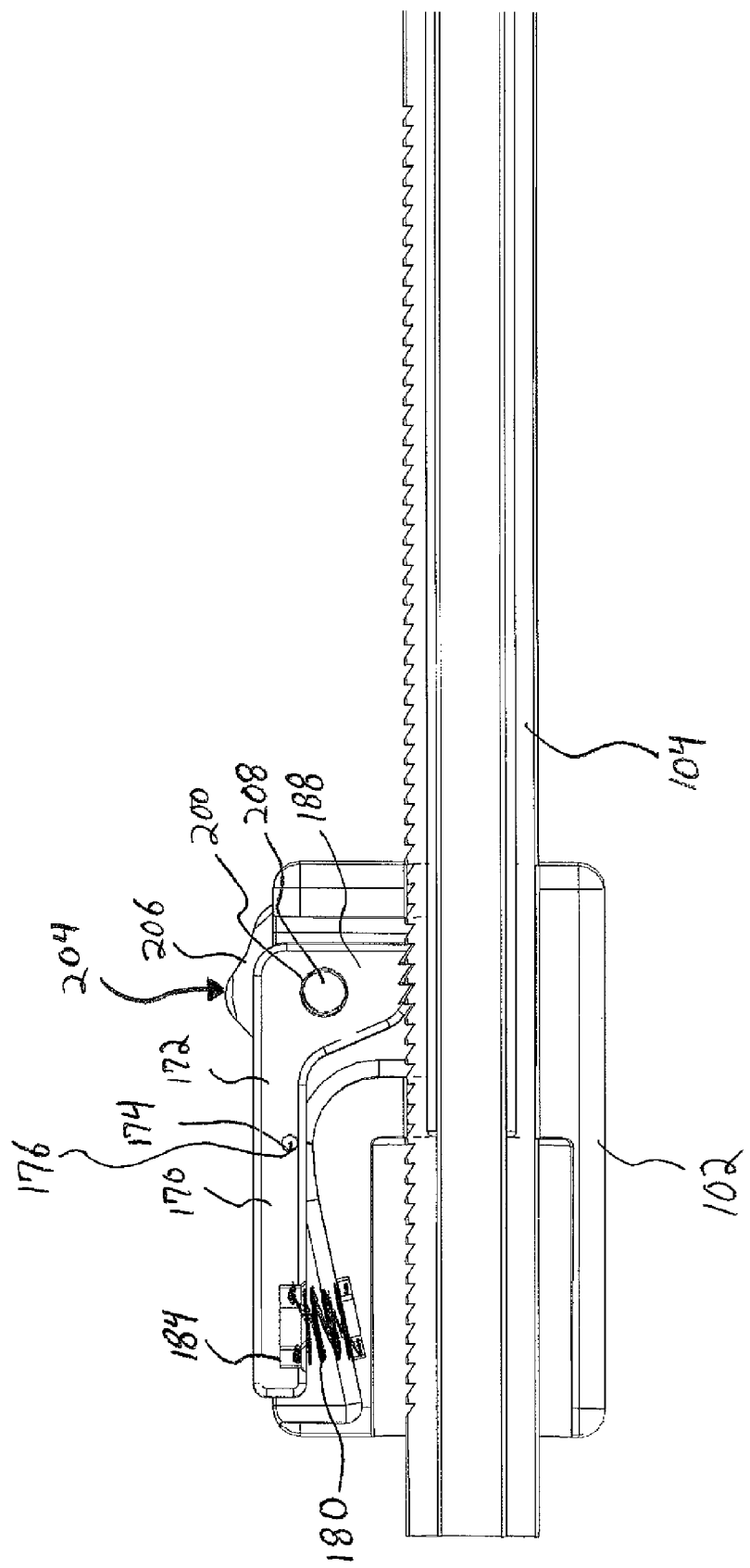
FIG. 8 is a magnified view of the ratchet box and internal components shown in FIG. 3.

The exemplary embodiments of the present disclosure are described and illustrated below to encompass to devices and methods utilized in fracture reduction and, more specifically, to devices and methods providing length adjustment during fracture fixation. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Referencing FIGS. 1-17, a first exemplary ratcheting strut 100 comprises a ratchet box 102 having a longitudinal opening extending therethrough that accommodates throughput of a ratchet tube 104. In exemplary form, the longitudinal opening is partially defined by a first cylindrical interior wall 106 having a first diameter. A series of fins 110, 112 are mounted to the interior wall 106 and extend into the interior of the longitudinal opening, thereby decreasing the cross-sectional area of the opening. In particular, each fin 110, 112 extends perpendicularly from the interior wall and includes an arcuate edge that matches the arcuate contour of the interior wall 106. An innermost edge of each fin 110, 112 comprises a geometric chord, where the horizontal cross-section of the interior wall 106 is circular. In this exemplary embodiment, a first pair of fins 110 is diametrically positioned opposite one another to create a horizontal cross-section having a constant width between the opposed pair of fins. Likewise, a second pair of fins 112 is mounted identically to the interior wall 106 as the first pair of fins, but is longitudinally spaced from the first pair of fins. Working together, the interior wall 106 and fins 110, 112 allow longitudinal traversal of the ratchet tube 104, while inhibiting axial rotation of the ratchet tube.

In this exemplary embodiment, the ratchet tube 104 comprises a cylindrical ring body having a cylindrical exterior surface 120 axially outset from a cylindrical interior surface 122. In this manner, the interior of the ratchet tube 104 is hollow and has a constant vertical, circular cross-section along its longitudinal length. An exterior surface of the ratchet tube 104 includes the cylindrical exterior surface 120, as well as a pair of planar surfaces 124 extending longitudinally along a majority of the longitudinal length of the ratchet tube. In exemplary form, these planar surfaces 124 may be formed by planarizing opposing sides of the ring body (i.e., hollow cylindrical tube) to remove material from the outside of the ring body, thereby decreasing the wall thickness of the ring body, but not impacting the dimensions of the cylindrical interior surface 122. In exemplary form, the material removed from the ring body can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 124, in exemplary form, do not extend along the entire longitudinal length of the ratchet tube 104, therefore a distal end 126 of the ratchet tube is cylindrical, while the opposing proximal end 128 of the ratchet tube is partially cylindrical. More specifically, a pair of arcuate surfaces 132, 134 extends between the planar surfaces 124 to partially define the exterior of the ratchet tube. Each arcuate surface 132, 134 is separated from the other cylindrical surface by approximately ninety rotational degrees, except for the distal end 126 where the cylindrical surfaces seamlessly intersect with the cylindrical exterior surface 120. The dorsal arcuate surface 132 also includes a series of angled depressions 136 that are longitudinally repeated and consistently spaced apart from one another to create a series of angled teeth 138 that are longitudinally inset from the distal and proximal ends 126, 128 of the ratchet tube 104. In exemplary form, each tooth 138 includes a vertical distal surface 144 and an inclined proximal surface 146 that intersects the distal surface to form a horizontal peak 148. As will be discussed in more detail hereafter, the inclined nature of the proximal surface 146 cooperates with a corresponding surface of a repositionable lever 170 to allow ratcheting action between the lever and the ratchet tube 104.

The shape of the ratchet tube 104 allows it to be inserted into the longitudinal opening of the ratchet box 102 so that the proximal end 124 of the ratchet tube 104 is inserted into a proximal opening 156 of the ratchet box 102 and extends through a distal opening 154 prior to insertion of the distal end 126 of the ratchet tube into the interior of the ratchet box. The distal opening 156 is defined by a second cylindrical interior wall 160 having a diameter larger than the first cylindrical interior wall 106. This second cylindrical interior wall 160 extends proximally until terminating at a distal flange 162 that extends between the cylindrical interior walls 106, 160. It should be noted that the cylindrical interior walls 106, 160 are coaxial with one another so that the distal flange 162 has a constant circular cross-section and axial depth. In this exemplary embodiment, the distal flange 162 is operative to inhibit throughput of objects having a diameter larger than the diameter of the first cylindrical interior wall 106. In addition, the fins 110, 112 located on the interior of the first cylindrical interior wall 106 change the longitudinal profile of the longitudinal opening and prohibit throughput of cylindrical objects having a diameter slightly less than the diameter of the first cylindrical interior wall. As mentioned previously, the distal end 126 of the ratchet tube 104 is cylindrical and exhibits a constant exterior diameter, whereas the proximal end 128 and a majority of the longitudinal length of the ratchet tube exhibits a cross-section that is circular with respect to the arcuate surfaces 132, 134, but is rectangular with respect to the planar surfaces 124. This dual shape (circular and rectangular) profile is also consistent with the dual shape profile on the interior of the cylindrical interior wall 106 taking into account the fins 110, 112. In exemplary form, the exterior diameter (between the arcuate surfaces 132, 134) of the ratchet tube 104 is slightly less than the internal diameter of the cylindrical interior wall 106. Likewise, the horizontal width between the opposed fins 110, 112 is slightly larger than the horizontal distance between the planar surfaces 124. As a result, the proximal end 128 of the ratchet tube 104 is able to be longitudinally repositioned along the entire length of the longitudinal opening of the ratchet box 102, whereas the distal end 126 of the ratchet tube is able to be longitudinally repositioned within only a portion of the longitudinal opening because the distal end cannot pass beyond the fins 110, 112. In this manner, when the proximal end 128 of the ratchet tube 104 is first inserted into the distal opening 156 of the ratchet box 102 and longitudinally repositioned proximally, eventually the distal end 126 of the ratchet tube (where the planar surfaces 124 terminate and the uniform circumferential surface begins) abuts the fins 110, which prohibit further proximal motion of the ratchet tube.

In order to fix the position of the ratchet tube 104 with respect to the ratchet box 102, the lever 170 is repositionably mounted to the ratchet box to selectively engage the ratchet tube. More specifically, the lever 170 comprises an L-shaped beam 172 having a cylindrical pivot orifice 174 that accepts a dowel 176 concurrently seated within a cylindrical dowel orifice 178 in order to mount the lever 170 to the ratchet box 102. In exemplary form, the dowel 176 is cylindrical and has an external diameter that is slightly larger than the internal diameter of the cylindrical dowel orifice 178, thus securing the dowel in position via a friction fit. In contrast, the diameter of the cylindrical pivot orifice 174 is slightly larger than the external diameter of the dowel 176, thereby allowing pivoting motion of the lever 170 around the dowel.

In this exemplary embodiment, the lever 170 is biased by a spring 180 to engage the ratchet tube 104. More specifically, the coil spring 180 is seated within a spring receiver 182 of the ratchet box 102. The spring receiver 182 comprises a ring-shaped depression that circumscribes a cylindrical projection that is adapted to be partially inserted into one end of the coil spring 180. Similarly, the underside of the lever 170 also includes a spring receiver 184 that likewise comprises a ring-shaped depression that circumscribes a cylindrical projection adapted to be partially inserted into the other end of the coil spring 180. The bias of the coil spring 180 is selected or set so that when no affirmative pressure is applied by a user to the lever 170, a head 188 of the lever contacts the ratchet tube 104. In exemplary form, the head 188 of the lever 170 includes a series of angled teeth 192 that are each formed by the interaction of a vertical proximal surface 194 and an inclined distal surface 196 that intersects the proximal surface to form a peak 198. In this fashion, the angled teeth 192 of the lever 170 are inclined to match the incline of the angled teeth 138 of the ratchet tube 104. As a result, when no affirmative pressure is applied by a user to the lever 170, the ratchet tube 104 may be repositioned proximally so that the inclined surfaces 146, 196 ride upon one another (and overcome the spring 180 bias to raise the lever 170) successively, thereby allowing the peaks 148, 198 to pass one another. In contrast, when no affirmative pressure is applied by a user to the lever 170, the ratchet tube 104 may not be repositioned distally because the vertical surfaces 144, 194 contact one another and do not allow distal motion because the lever remains in the line of travel of the ratchet tube. Accordingly, in order to reposition the ratchet tube 104 distally, a user needs to apply affirmative pressure to the lever 170 and overcome the spring 180 bias, thereby removing the lever from the line of travel of the ratchet tube. When the appropriate distal travel is reached, the user simply discontinues affirmative pressure to the lever 170, thereby allowing the spring 180 bias to dominate and cause the lever to contact the ratchet tube 104 so that the vertical surfaces 144, 194 contact one another and do not allow distal motion.

The lever 170 may also be locked in position so that the angled teeth 192 engage the angled teeth 138 of the ratchet tube 104. In order to lock the lever 170 in the position shown in FIG. 3, the lever includes a lock orifice 200 that is sized to receive a portion of a thumb screw 204. The thumb screw 204 includes a knob 206 mounted to a perpendicularly extending, linear projection 208 having threads 210 adapted to engage threads 212 on the inside of a thumb screw orifice 214 extending through the ratchet box 102. When the projection 208 of the thumb screw 204 is inserted through the thumb screw orifice 214 and lock orifice 200, the lever 170 is not pivotally repositionable so that the teeth 192 of the lever are out of the line of travel of the teeth 138 of the ratchet tube 104. Consequently, to pivot the lever 170 so that the teeth 192 of the lever 170 are out of the line of travel of the teeth 138 of the ratchet tube 104, the thumb screw 204 needs to be positioned so that the projection 208 is no longer received within the lock orifice 200. After the thumb screw 204 is positioned so that the projection 208 is no longer received within the lock orifice 200, the lever 170 may be repositioned by application of affirmative pressure to overcome the bias of the spring 180, thereby pivoting the lever so that the teeth 192 of the lever are out of the line of travel of the teeth 138 of the ratchet tube 104.

When the ratchet tube 104 is repositioned with respect to the ratchet box 102, other components mounted to the ratchet tube are also repositioned. In this exemplary embodiment, a tube mount 220 is coupled to the proximal end 128 of the ratchet tube via a friction fit. It should be understood, however, that other means of attachment may be used such as, without limitation, adhesives, set screws, and welds. In this manner, longitudinal motion of the ratchet tube 104 causes longitudinal motion of the tube mount 220 and vice versa. The tube mount 220 includes a through opening 222 that accommodates longitudinal movement of the ratchet tube 104 independent of movement of the tube mount. A distal end 224 of the tube mount includes a cylindrical collar 226 that circumscribes the proximal end 128 of the ratchet tube 104. On the interior of this collar 226 is a flange 228 that provides an abutment surface against which the exposed proximal end 128 of the ratchet tube contacts when fully seated within the collar. The flange 228 also operates to change the profile of the through opening 222 from circular along the collar 226, to a narrower hybrid profile. This hybrid profile is defined by a pair of parallel, planar surfaces 230 bridged by a pair of arcuate surfaces 232 that extend longitudinally along a sleeve 236 integrally formed with the flange 228 and collar 226. An exterior surface of the sleeve 236 is cylindrical and smooth, but for a circumferential trench 240 and a radial through opening 242, where the radial through opening extends into the through opening 222 but the circumferential trench does not. The trench 240 is adapted to partially receive a set screw mounted to a nut 250 that is mounted to and rotationally repositionable with respect to the tube mount 220.

In exemplary form, the nut 250 circumscribes a portion of the sleeve 236 and is rotationally repositionable with respect to the sleeve. The nut also includes one or more set screw orifices 252 open to the cylindrical exterior surface 254 that extend into a hollow interior 258, which includes proximal and distal openings 260, 262. The exterior surface 254 also includes a pair of rounded projections 266 that are utilized to grasp the nut 250 and facilitate rotation of the nut with respect to the sleeve 236. In this exemplary embodiment, the distal opening 262 allows access to a cylindrical cavity defined by a circumferential interior wall 268. At the proximal end of this interior wall 268 is a flange 272 that provides an abutment surface against which the exposed proximal end of the sleeve 236 contacts when fully seated within the nut 250. The flange 272 also operates to change the profile of the hollow interior 258 from circular along the interior wall 268, to a narrower hybrid profile. This hybrid profile is defined by a pair of parallel surfaces 276 tapped to create threads and bridged by a pair of arcuate surfaces 278 that extend longitudinally until reaching a proximal end 280 of the nut 250. The parallel, tapped surfaces 276 are adapted to be engaged by a threaded post 284 that extends through the nut 250, the tube mount 220, and partially through an interior of the ratchet tube 104.

By way of example, the threaded post 284 comprises a cylinder having a cylindrical exterior surface 286, as well as a pair of planar surfaces 288 extending longitudinally along a majority of the longitudinal length of the threaded post. In exemplary form, these planar surfaces 288 may be formed by planarizing opposing sides of the cylinder to remove material from the exterior, thereby decreasing the thickness of the cylinder at certain circumferential locations. In exemplary form, the material removed from the cylinder can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 288, in exemplary form, do not extend along the entire longitudinal length of the threaded post 284 so that a distal end 292 of the threaded post retains a cylindrical shape, while the opposing proximal end 294 of the threaded post is partially cylindrical. More specifically, a pair of cylindrical surfaces 296 extends between the planar surfaces 288 to partially define the exterior of the ratchet tube. Each cylindrical surface 296 is separated from the other cylindrical surface by approximately ninety rotational degrees, except for the distal end where the cylindrical surfaces seamlessly intersect with the cylindrical exterior surface 286. Both cylindrical surfaces 296 are tapped along a predetermined length that extends to the proximal end 294 to provide a series of repeating, partial threads 298. It is these partial threads 298 that are adapted to engage the tapped surfaces 276 of the nut 250 so that rotational repositioning of the nut results in longitudinal repositioning of the threaded post 284. More specifically, clockwise rotation of the nut 250 may reposition the threaded post 284 longitudinally in a distal direction, while counter-clockwise rotation of the nut 250 may reposition the threaded post 284 longitudinally in a proximal direction, or vice versa.

The distal end 292 of the threaded post 284 includes a cylindrical cavity that is tapped to provide internal threads 300. These threads 300 are adapted to be engaged by the threads 304 of a post cap 306. The post cap 306 includes a proximal cylindrical end 308 having threads 304 in order to mount the post cap to the threaded solid post 284. A solid distal end 312 of the post cap 306, integrally formed with the proximal end 308, is also cylindrical and includes a larger diameter than the proximal end. This larger diameter is slightly less than the diameter of the cylindrical interior surface 122 of the ratchet tube 104, thereby allowing the post cap to slide longitudinally within the interior of the ratchet tube. The distal end 312 also includes a circumferential trench 314 inset from the tip that is sized to accommodate a discontinuous friction sleeve 316. The discontinuous friction sleeve 316 is seated within the trench 314 and partially compressed by the cylindrical interior surface 122 of the ratchet tube 104. In a static environment, the outer diameter of the friction sleeve 316 is slightly larger than the diameter of the interior surface 122 of the ratchet tube 104. But when the friction sleeve 316 is seated within the trench 314 and inserted into the ratchet tube 104, the friction sleeve is circumferentially compressed to have an external diameter roughly equal to the diameter interior surface 122 of the ratchet tube. In this manner, the friction sleeve 316 creates frictional resistance against longitudinal repositioning of the sleeve with respect to the ratchet tube 104, which also creates resistance against longitudinal repositioning of the post cap 306 and threaded post 284 with respect to the ratchet tube. But this frictional resistance is not so great as to inhibit longitudinal motion of the sleeve 316, the post cap 306, and threaded post 284 when the nut 250 is rotated.

The proximal end 294 of the threaded post 284 is mounted to a ball joint 320 having a spherical ball end 322 integrally formed with a hollow cylinder 324. The hollow cylinder is threaded and these threads 328 are adapted to engage the partial threads 298 of the threaded post 284 in order to mount the threaded post to the ball joint 320.

The spherical ball end 322 of the ball joint 320 is rotationally and pivotally repositionable with respect to a socket cooperatively formed by a ball joint housing 330 and a ball joint cap 334. In exemplary form, the ball joint housing 330 comprises a casing that partially encapsulates the spherical ball end 322 of the ball joint 320. On the interior of this casing is a semispherical depression that provides a bearing surface against which the spherical ball end rotates and pivots. The ball joint housing 330 also includes a circular ring 336 integrally formed with the casing and having a diameter greater than the diameter of the spherical ball end. In order to retain the spherical ball end 322 within the ball joint housing 330, as well as selectively removing the spherical ball end from within the ball joint housing, the circular ring includes threads 340 that are adapted to engage threads 342 of the ball joint cap 334 to secure the ball joint cap to the ball joint housing via a friction fit.

Figure 16:
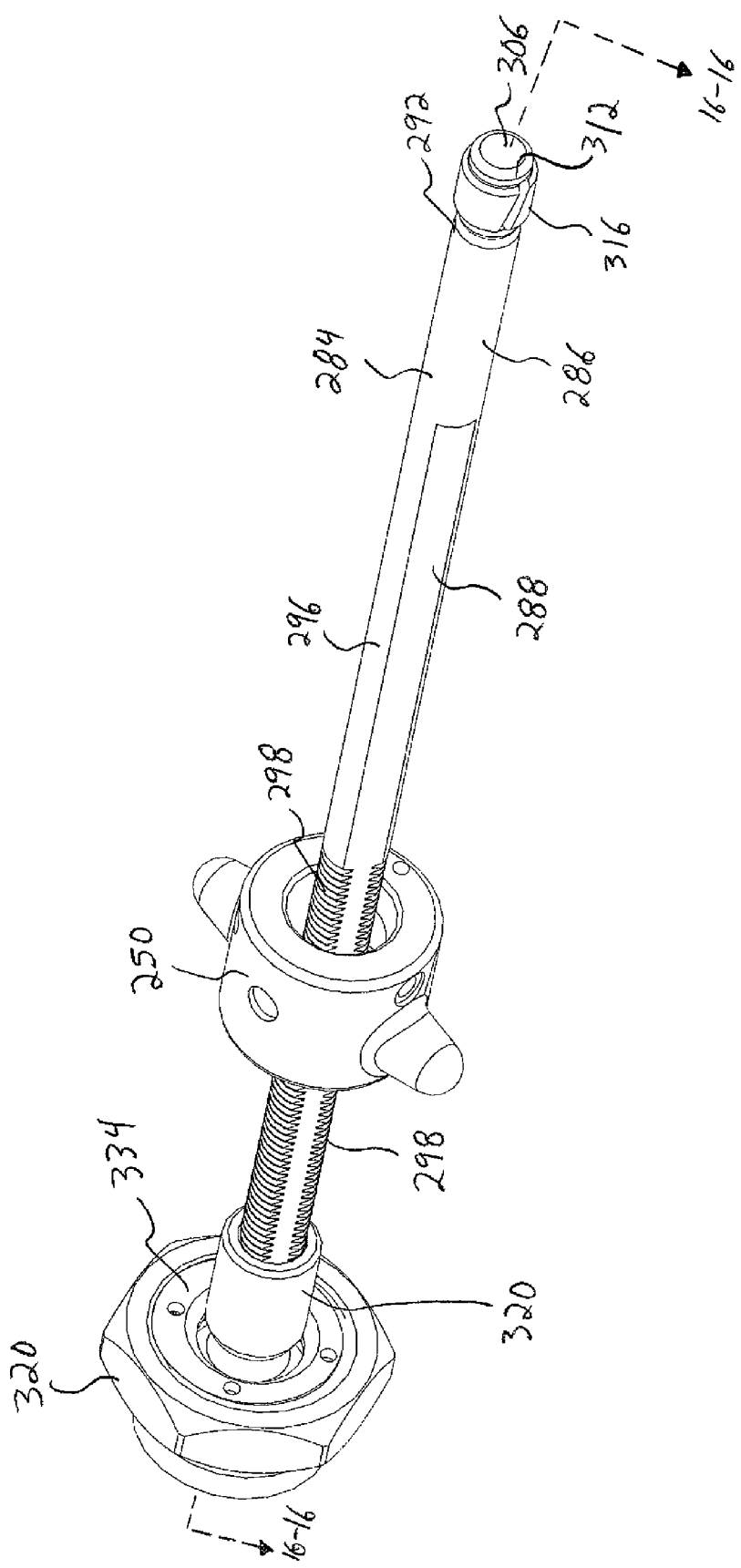
FIG. 16 is a cross-sectional view of the components of FIG. 10 taken along line 16-16.
Figure 11:
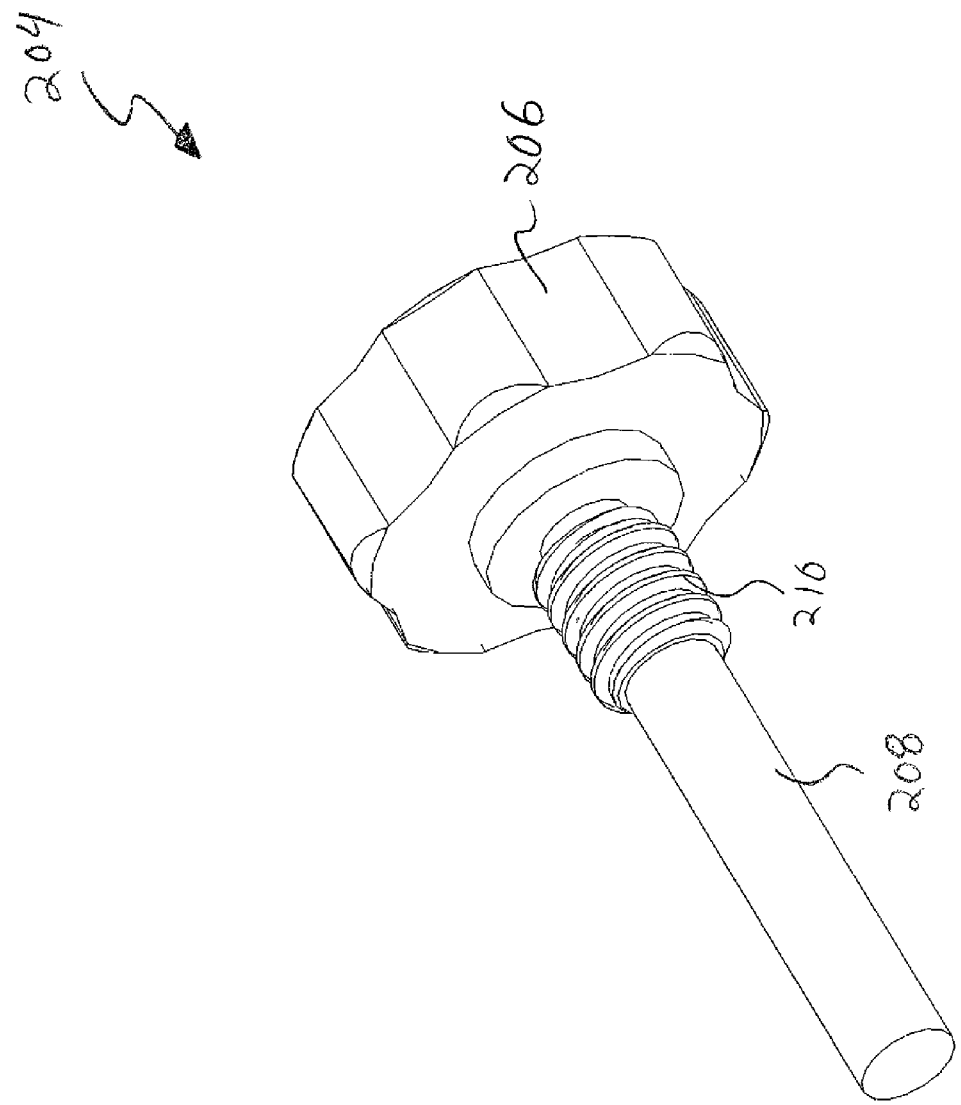
FIG. 11 is an elevated perspective view of the thumb screw in FIG. 1.
Figure 12:
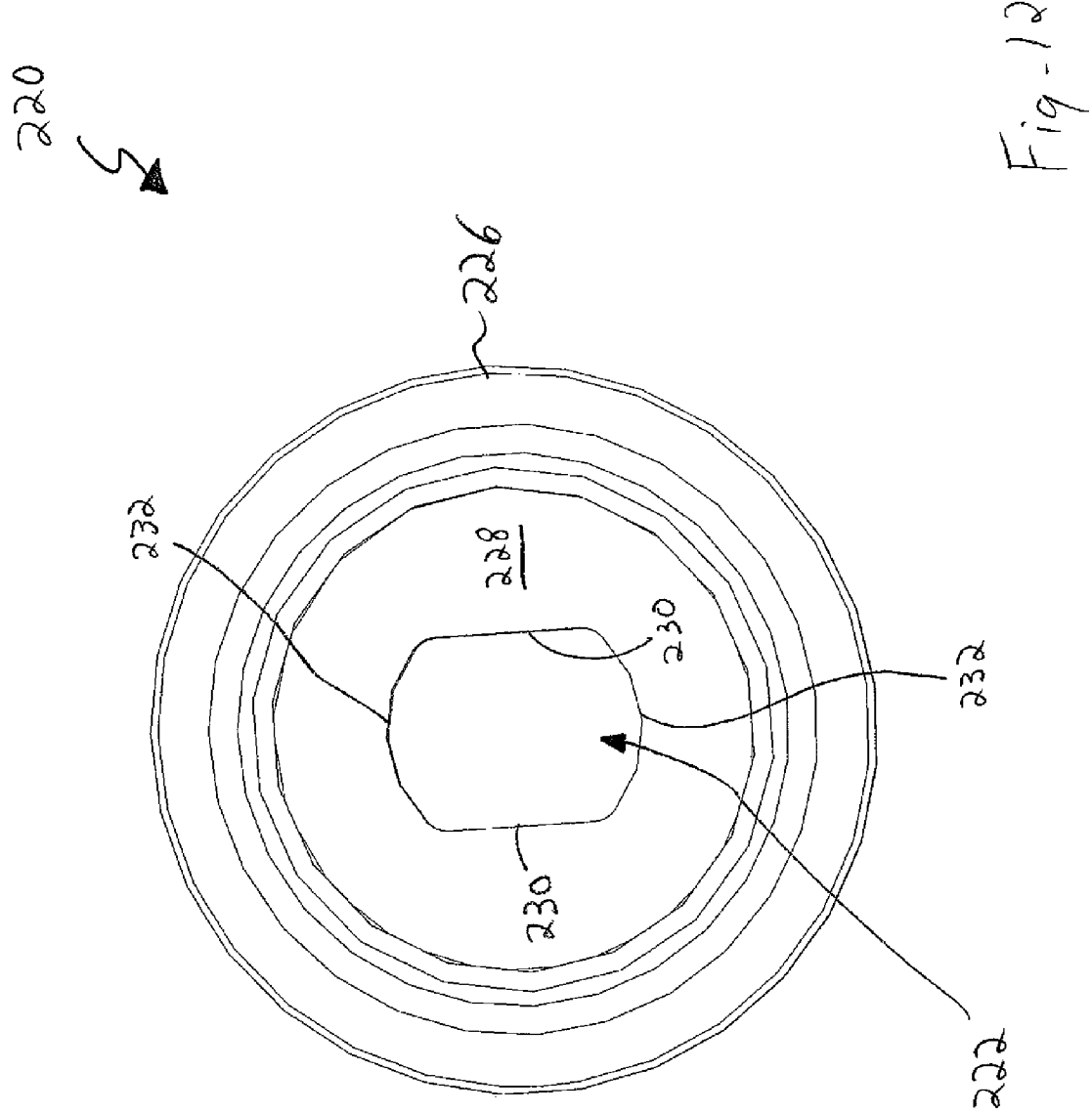
FIG. 12 is an end view of the tube mount of FIG. 1.
Figure 13:
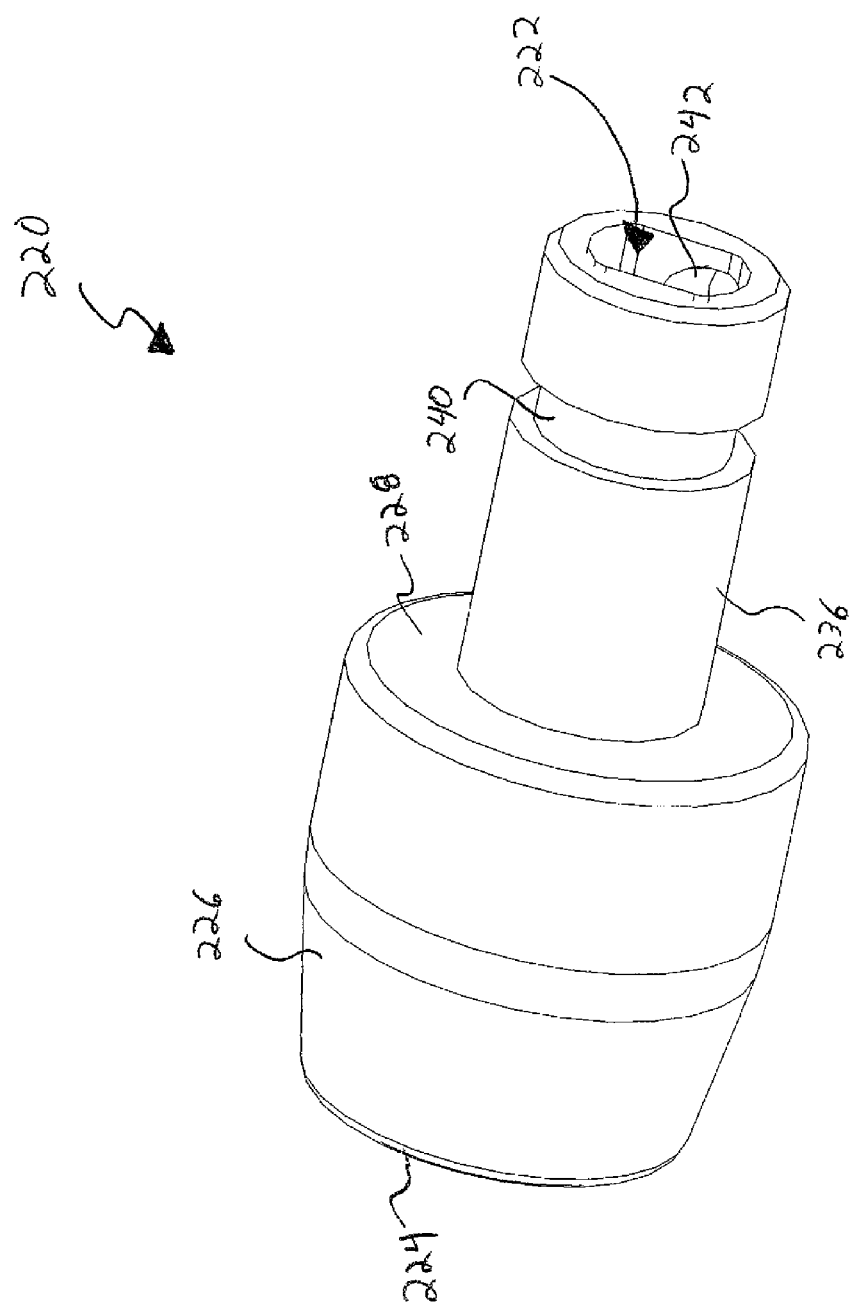
FIG. 13 is an elevated perspective view of the tube mount of FIG. 1.
Figure 14:
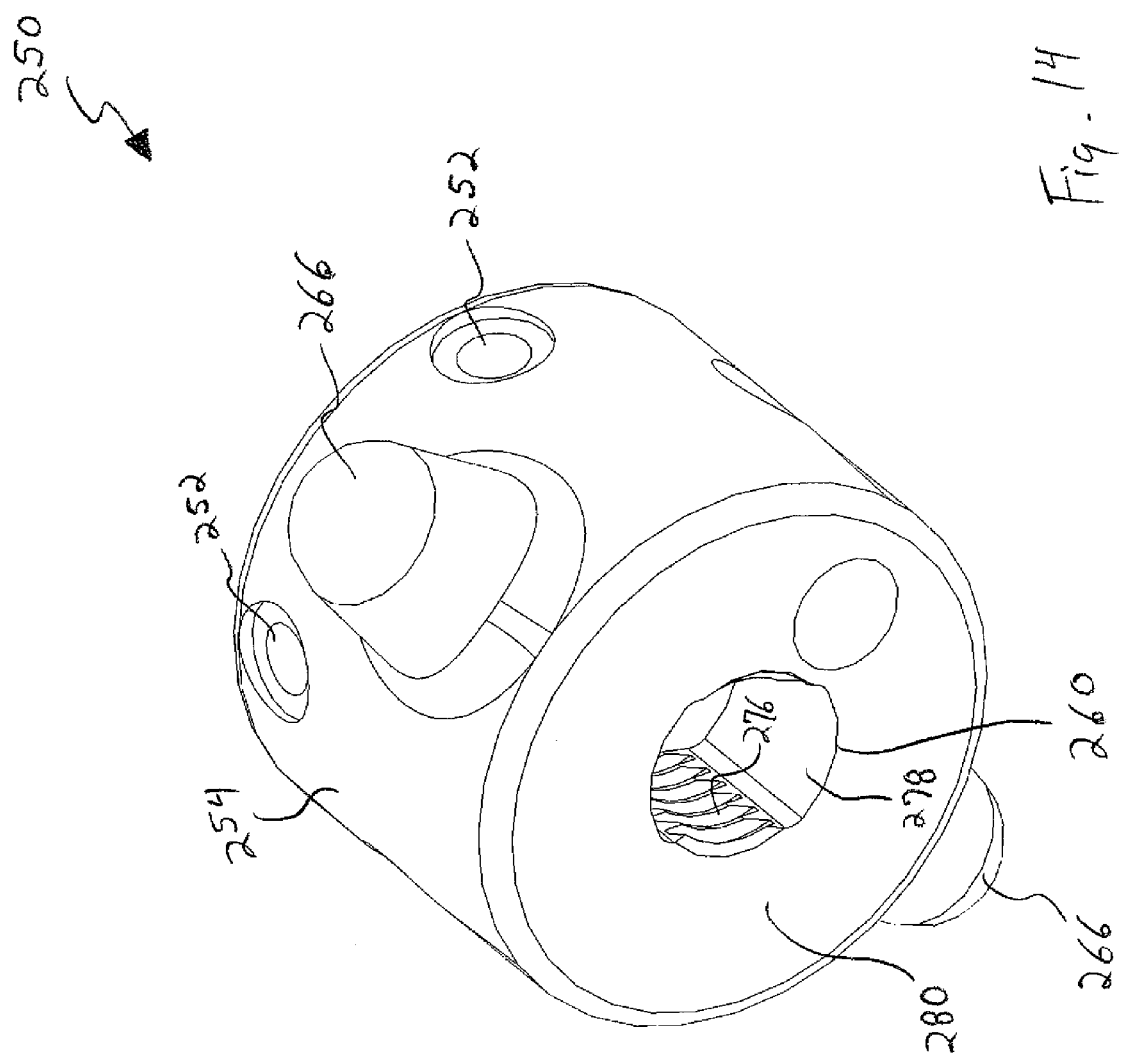
FIG. 14 is an elevated perspective view of the nut of FIG. 1.
Figure 15:
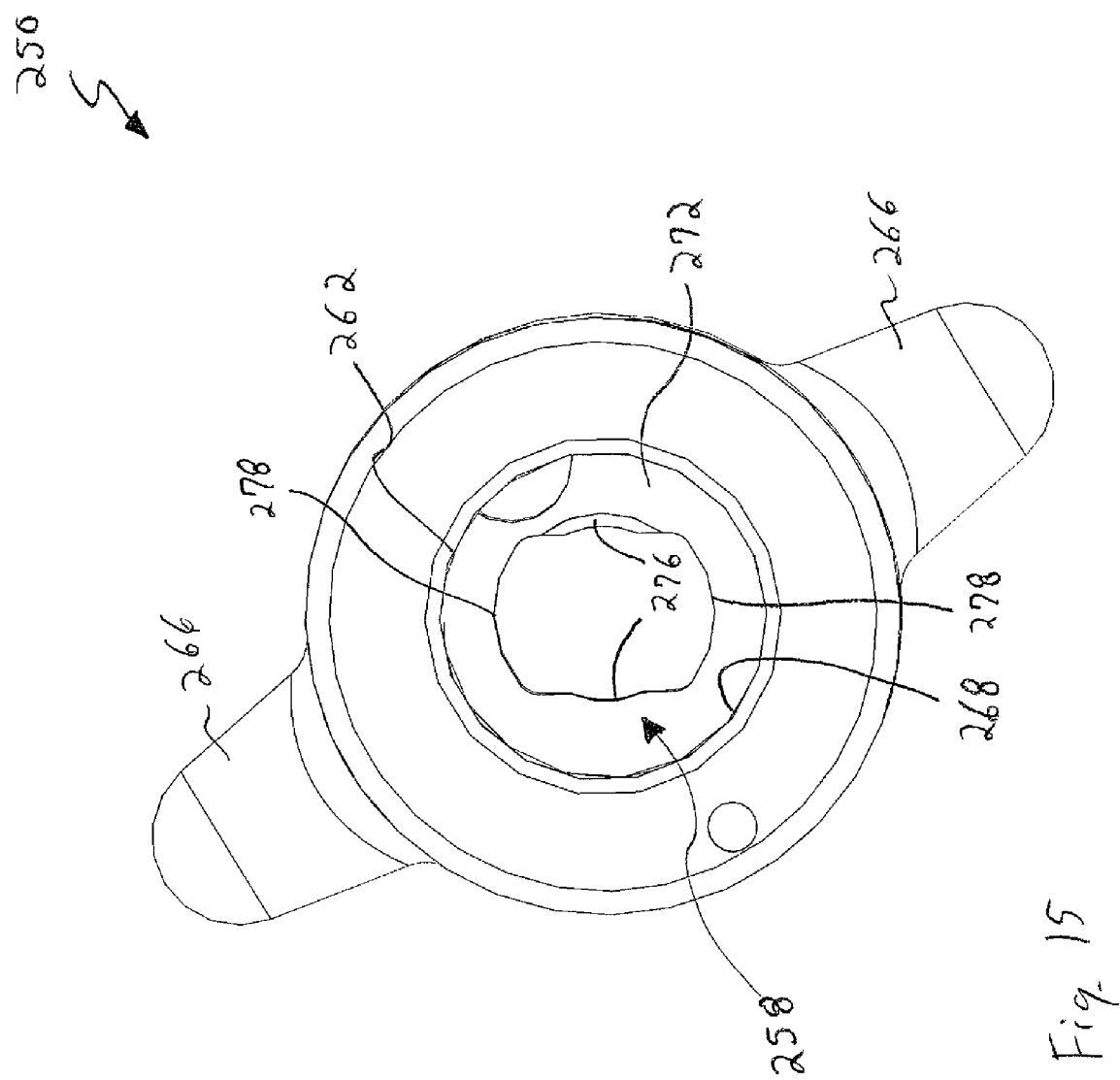
FIG. 15 is an end view of the nut of FIG. 1.
Figure 16:
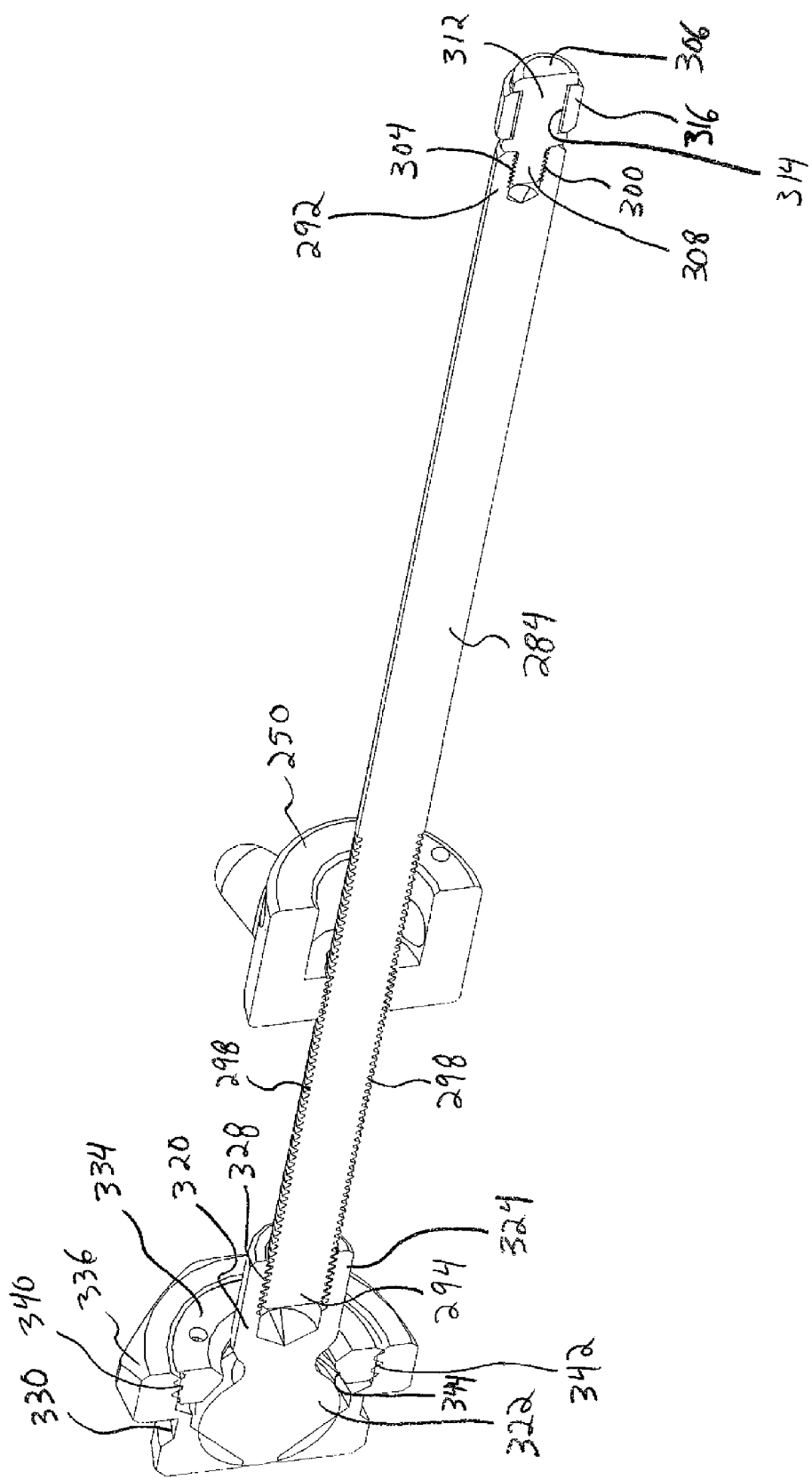

As shown in FIG. 16, the ball joint cap 334 is ring-shaped and includes a central opening defined by an arcuate circumferential surface 344. This arcuate circumferential surface 344 cooperates with the semispherical depression of the ball joint housing 330 to create the spherical socket within which the spherical ball end 322 is able to rotate and pivot. In this exemplary embodiment, the diameter of the central opening of the ball joint cap 334 is less than the diameter of the spherical ball end 322 within the ball joint housing 330 so that once the ball joint cap and ball joint housing are mounted to one another with the spherical ball end 322 located therein, removal of the spherical ball end is not possible without discontinuing the ball joint cap from being mounted to ball joint housing.

Referring back to FIGS. 5-7, as discussed previously, the distal end of the ratchet box 102 includes a distal opening 156 defined by the second cylindrical interior wall 160, which ends proximally when it meets the distal flange 162.

The distal opening is sized to accommodate throughput of the ratchet tube 104 as well as partial insertion of another tube 350. This second tube 350 is longitudinally cylindrical and includes a smooth exterior circumferential surface 352 that has a relatively constant diameter along the vast majority of the length of the second tube, but for the distal end 356. An interior of the second tube 350 is hollow and includes an opening 358 at a proximal end 360 of the second tube. This opening 358 provides access to a cylindrical cavity partially defined by interior circumferential wall 362 having a diameter large enough to accommodate the ratchet tube 104. In exemplary form, the proximal end 360 of the second tube 350 is inserted through the distal opening 156 of the ratchet box 102 and longitudinally repositioned until the proximal end 360 contacts the distal flange 162 on the inside of the ratchet box. It should be noted that the internal diameter of the second cylindrical interior wall 160 of the ratchet box 102 is slightly less than the external diameter of the second tube 350, thereby securing the second tube to the ratchet box via a friction fit.

The longitudinal profile of the second tube 350 is substantially constant until it changes when approximately reaching the distal end 356. Proximate the distal end 356, the interior circumferential wall 362 terminates at an internal, ring-shaped flange 366 operative to change the cross-section of the cavity. In particular, the flange 360 includes a central opening that feeds into a cylindrical cavity having a diameter less than that of the interior circumferential wall 362. This smaller diameter cylindrical cavity is partially defined by a threaded circumferential surface 370 that is adapted to engage a threaded circumferential surface 374 of a second ball joint 380. In contrast to the first ball joint 320 (see FIG. 2) that includes a female connection comprising a hollow cylinder having an internal circumferential surface 328 that is threaded, this second ball joint 380 include a male connection comprising an external circumferential surface 374 threaded to fit within and engage the threaded circumferential surface 370 of the smaller diameter cylindrical cavity of the second tube 350.

The second ball joint 380 comprises a spherical ball end 382 integrally formed with the male connection. This spherical ball end 382 of the ball joint 380 is rotationally and pivotally repositionable with respect to a socket cooperatively formed by a ball joint housing 390 and a ball joint cap 394. In exemplary form, the ball joint housing 390 comprises a casing that partially encapsulates the spherical ball end 382 of the ball joint 380. On the interior of this casing is a semispherical depression that provides a bearing surface against which the spherical ball end 382 rotates and pivots. The ball joint housing 390 also includes a circular ring 396 integrally formed with the casing and having a diameter greater than the diameter of the spherical ball end 382. In order to retain the spherical ball end 382 within the ball joint housing 390, as well as selectively removing the spherical ball end from within the ball joint housing, the circular ring includes threads 400 that are adapted to engage threads 402 of the ball joint cap 394 to secure the ball joint cap to the ball joint housing.

Figure 17:
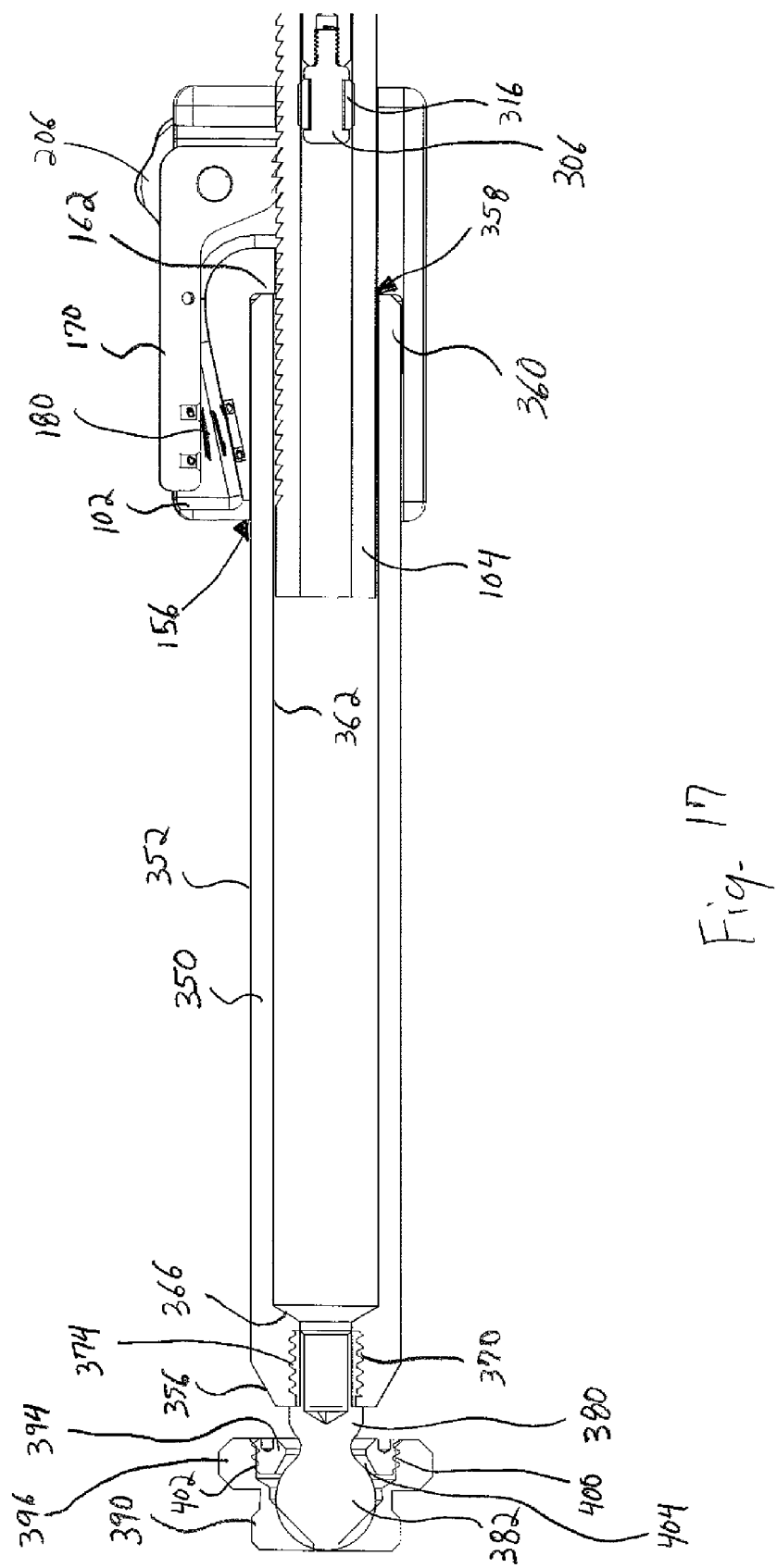
FIG. 17 is a magnified view of the ratchet box and other components shown in FIG. 3.
Figure 18:
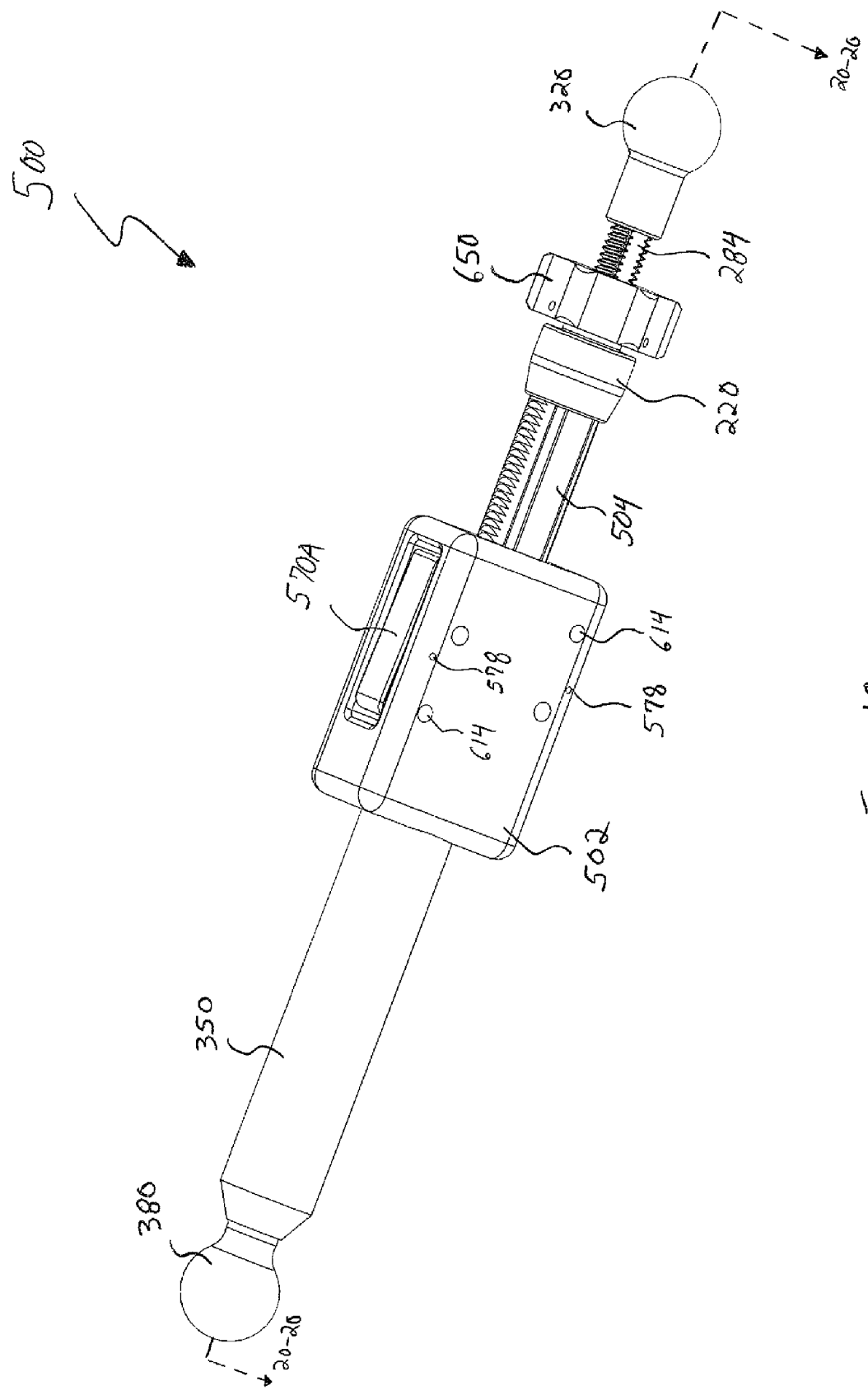
FIG. 18 is an elevated perspective view of an assembled second exemplary ratcheting strut in accordance with the instant disclosure.
Figure 19:
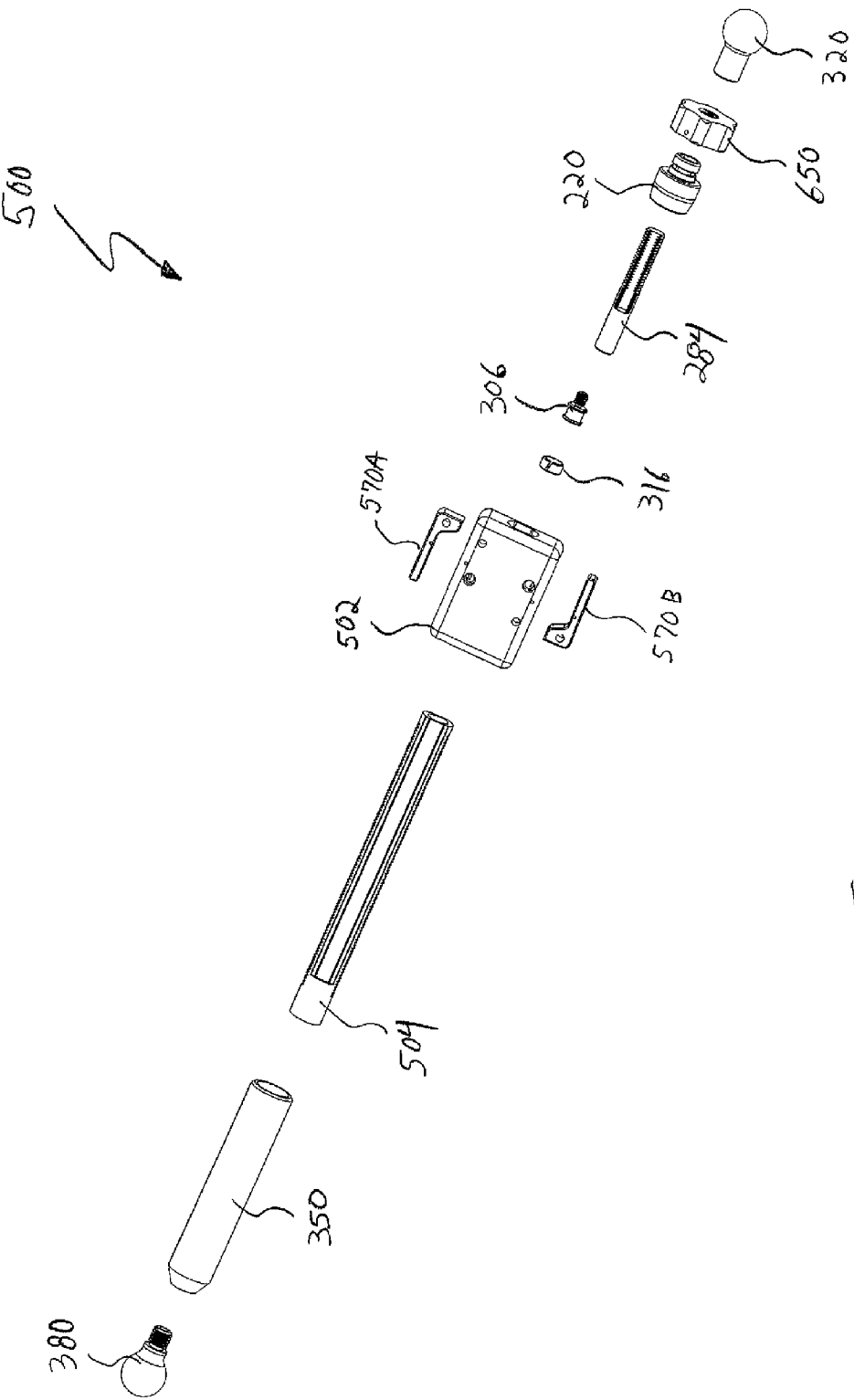
FIG. 19 is an exploded view of the second exemplary ratcheting strut of FIG. 18.
Figure 20:
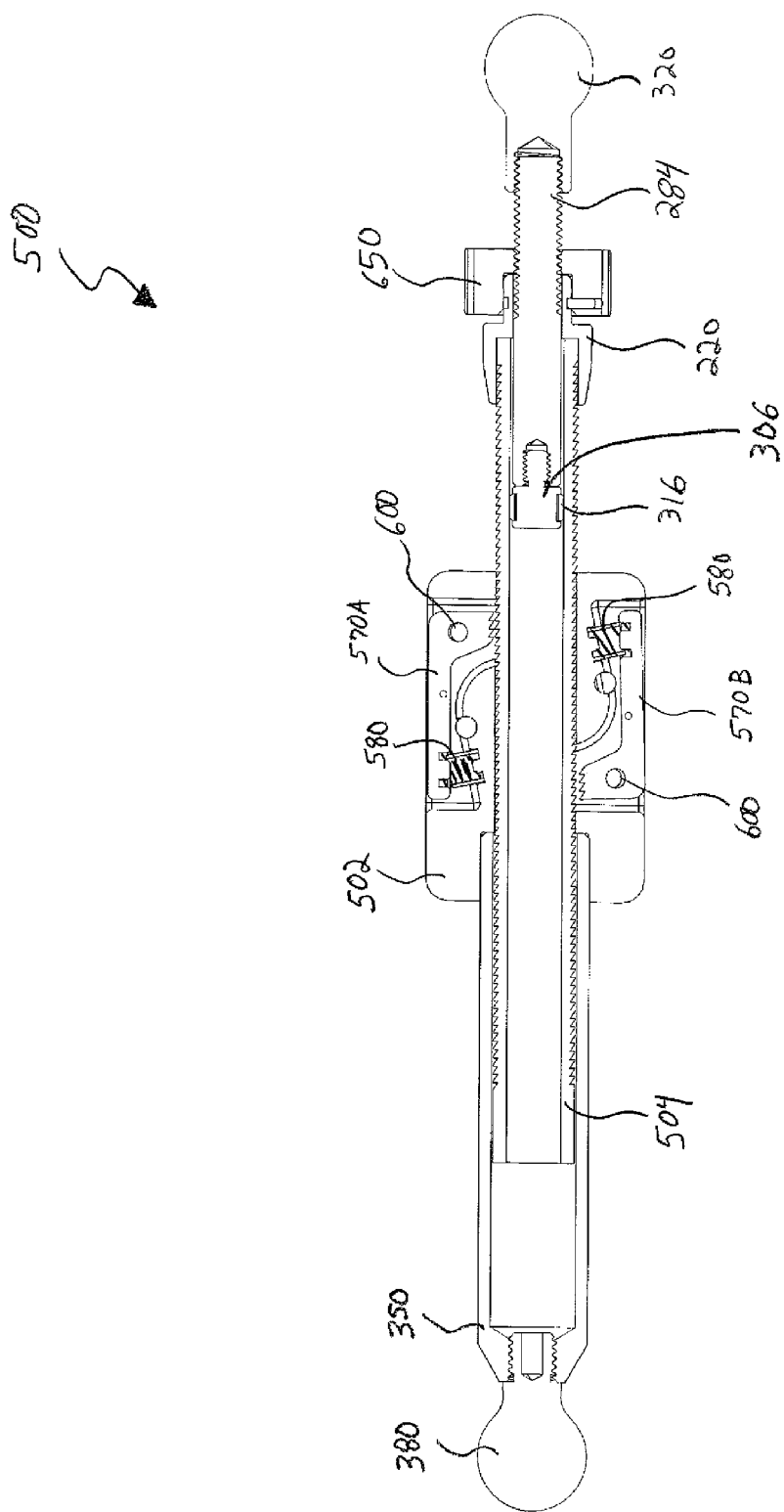
FIG. 20 is a cross-sectional view of the second exemplary ratcheting strut of FIG. 18 taken along line 20-20.
Figure 21:
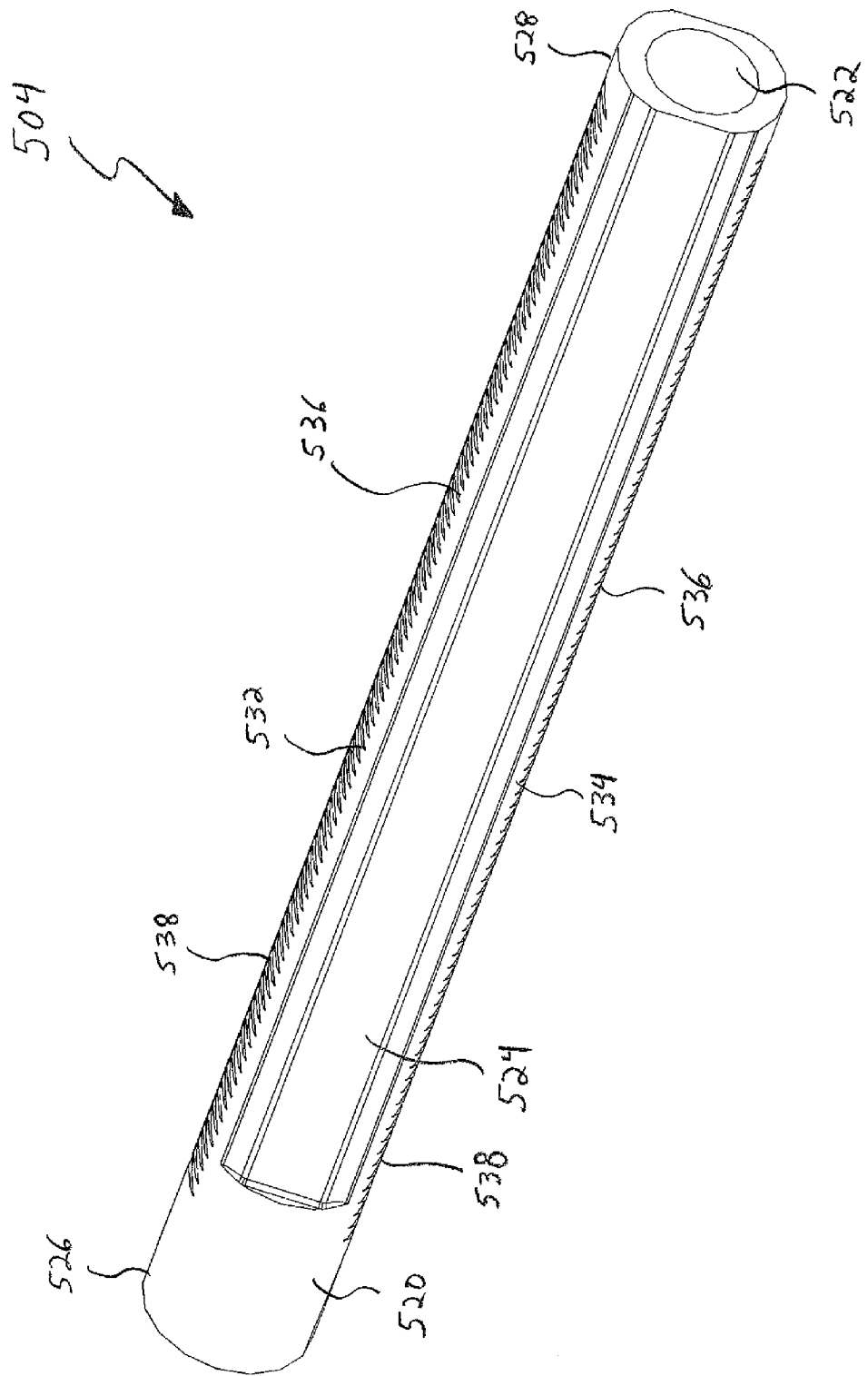
FIG. 21 is an elevated perspective view of the ratchet tube of FIG. 18.
Figure 22:
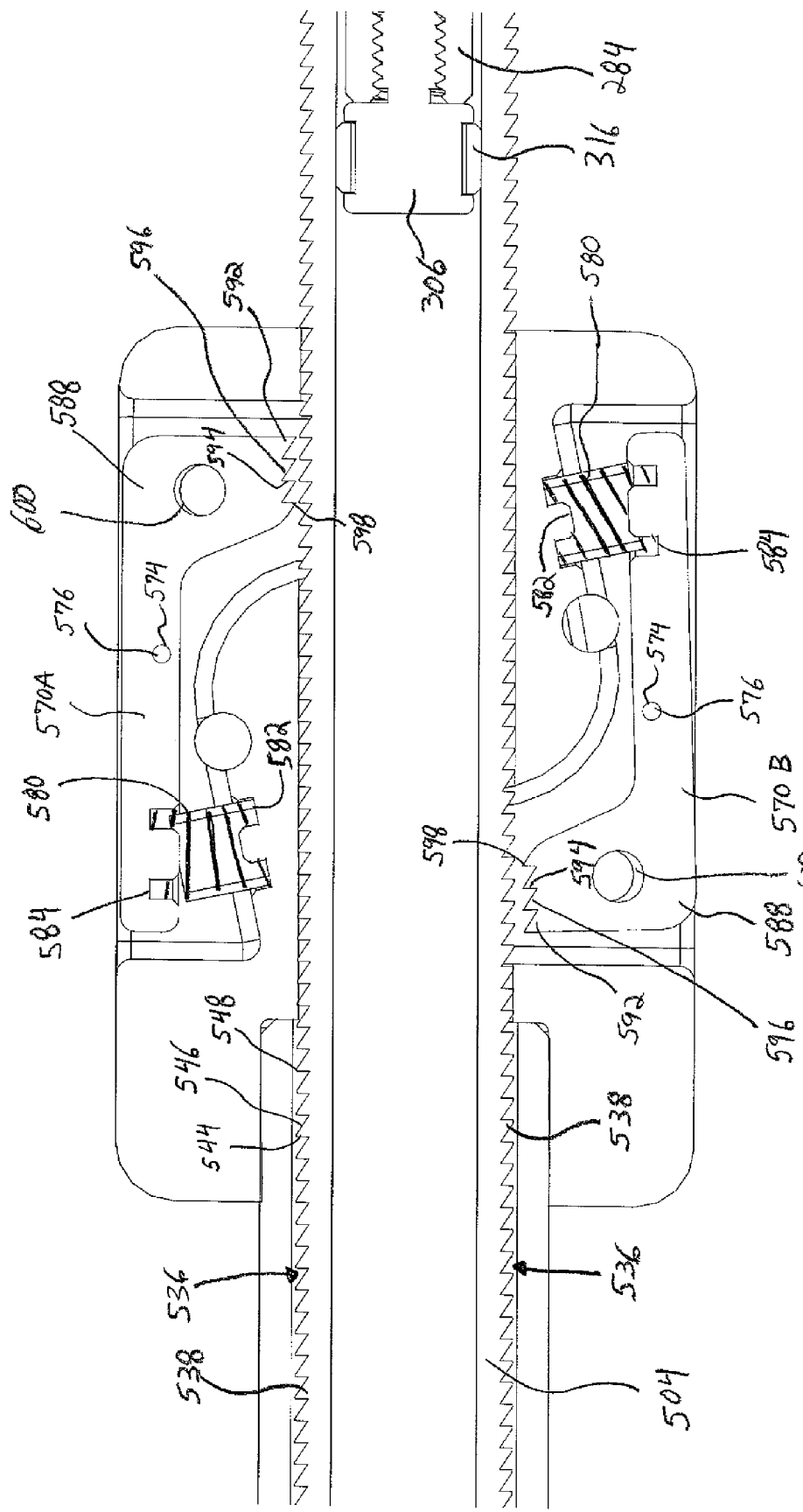
FIG. 22 is a magnified view of the ratchet box and internal components shown in FIG. 20.
Figure 23:
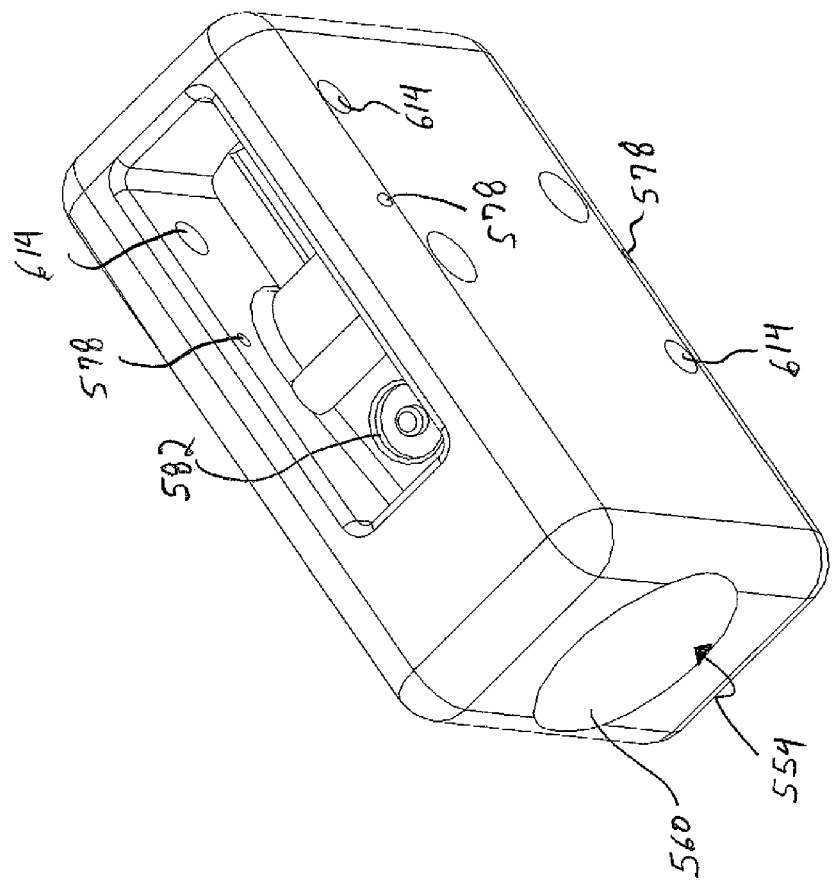
FIG. 23 is an elevated perspective view of the ratchet box of FIG. 18.
Figure 24:
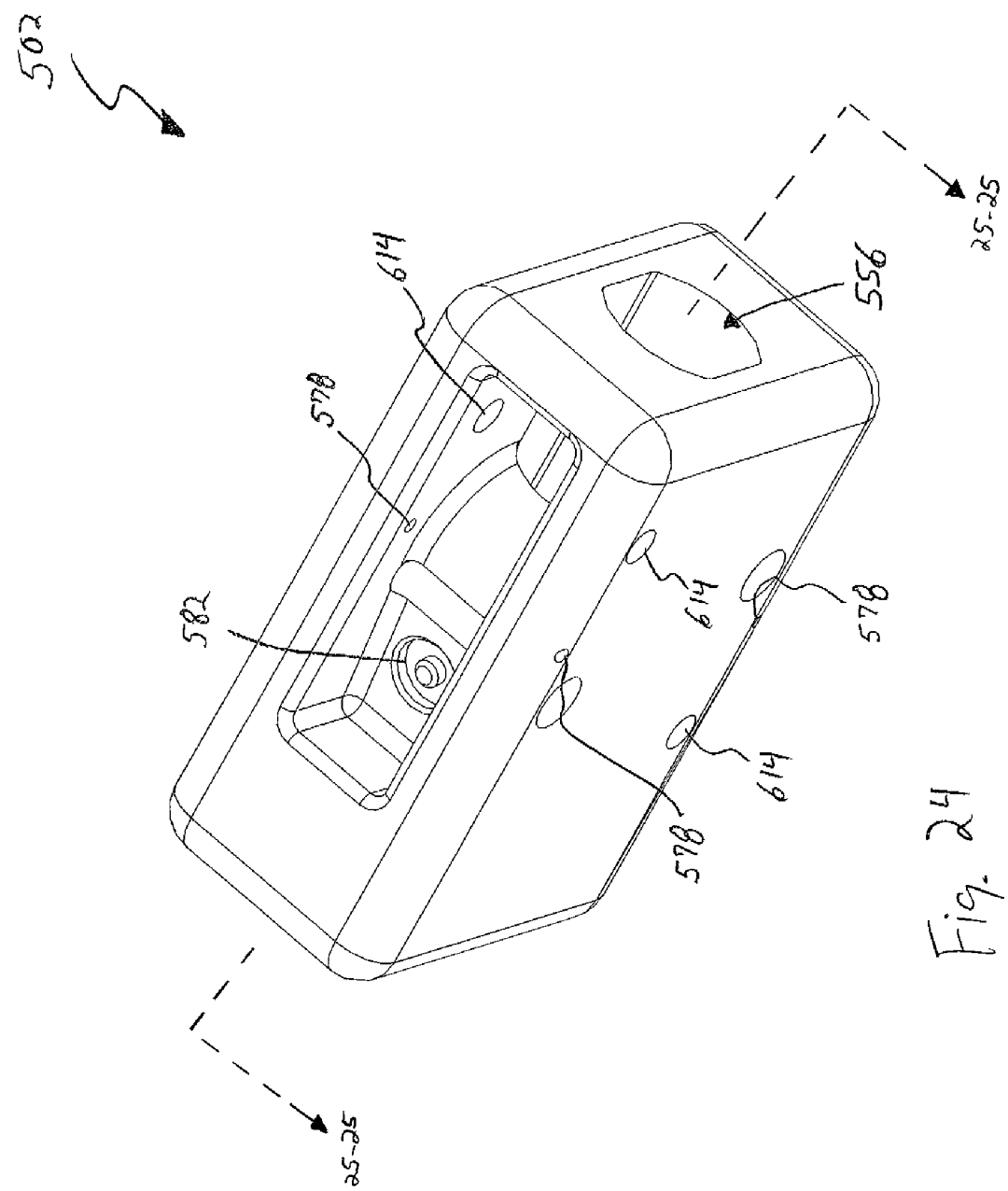
FIG. 24 is another elevated perspective view of the ratchet box of FIG. 18.
Figure 25:
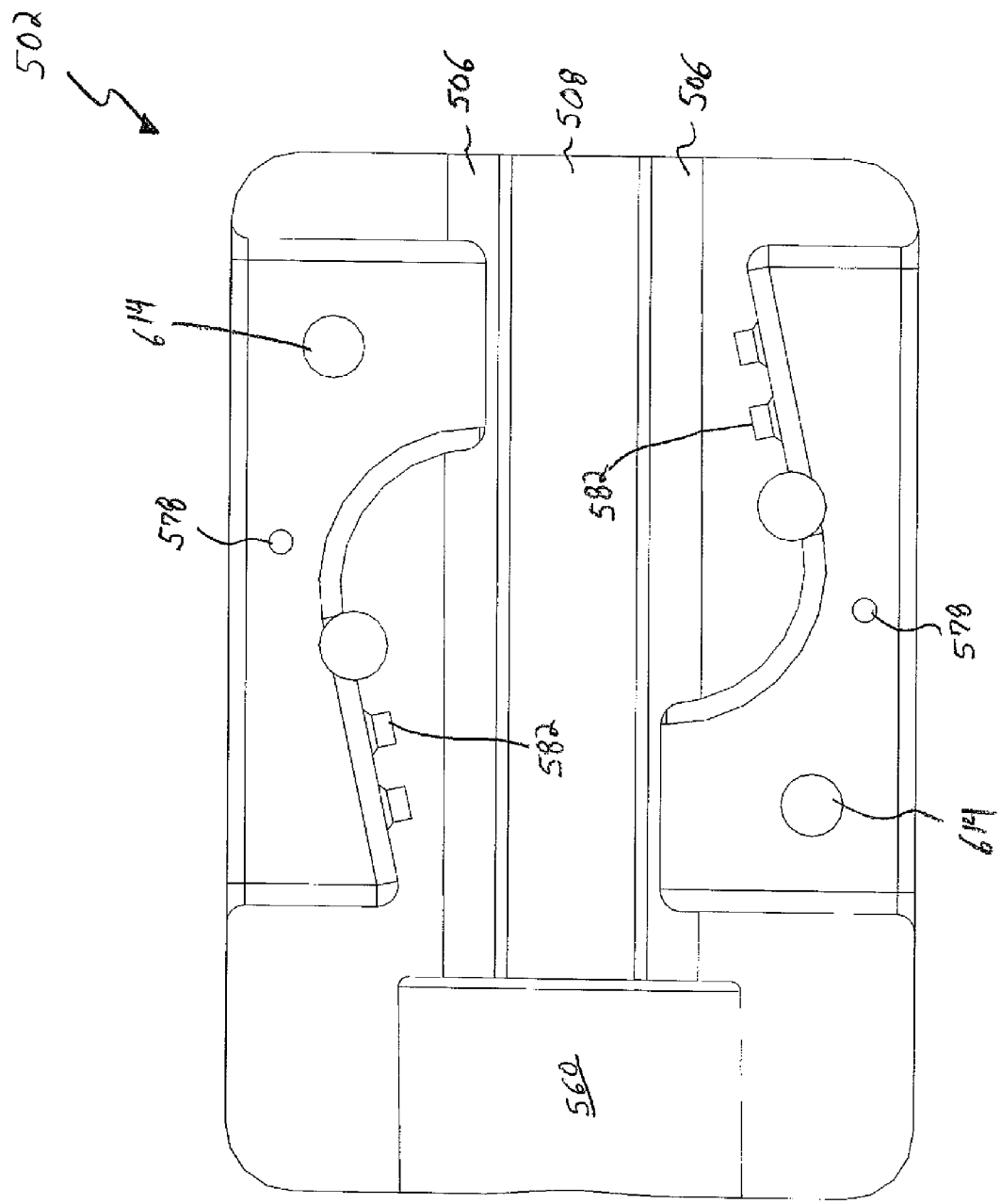
FIG. 25 is a cross-sectional view of the ratchet box of FIG. 20 taken along line 25-25.
Figure 26:
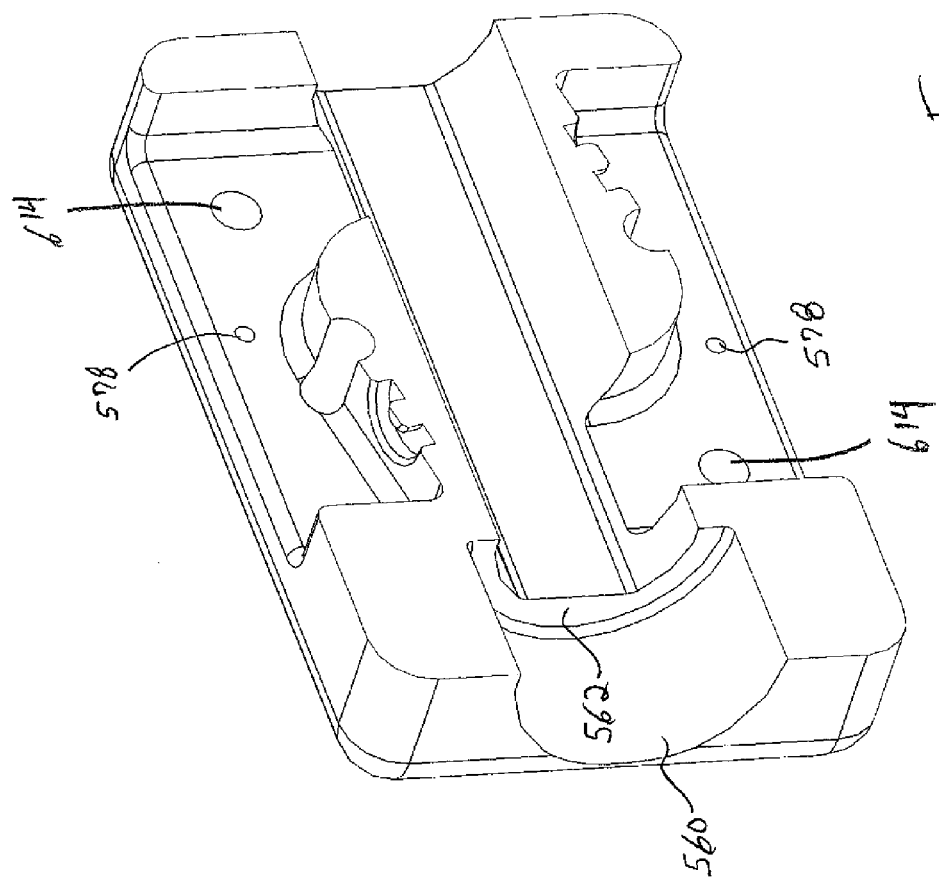
FIG. 26 is an elevated perspective view of the cross-section of FIG. 25.
Figure 27:
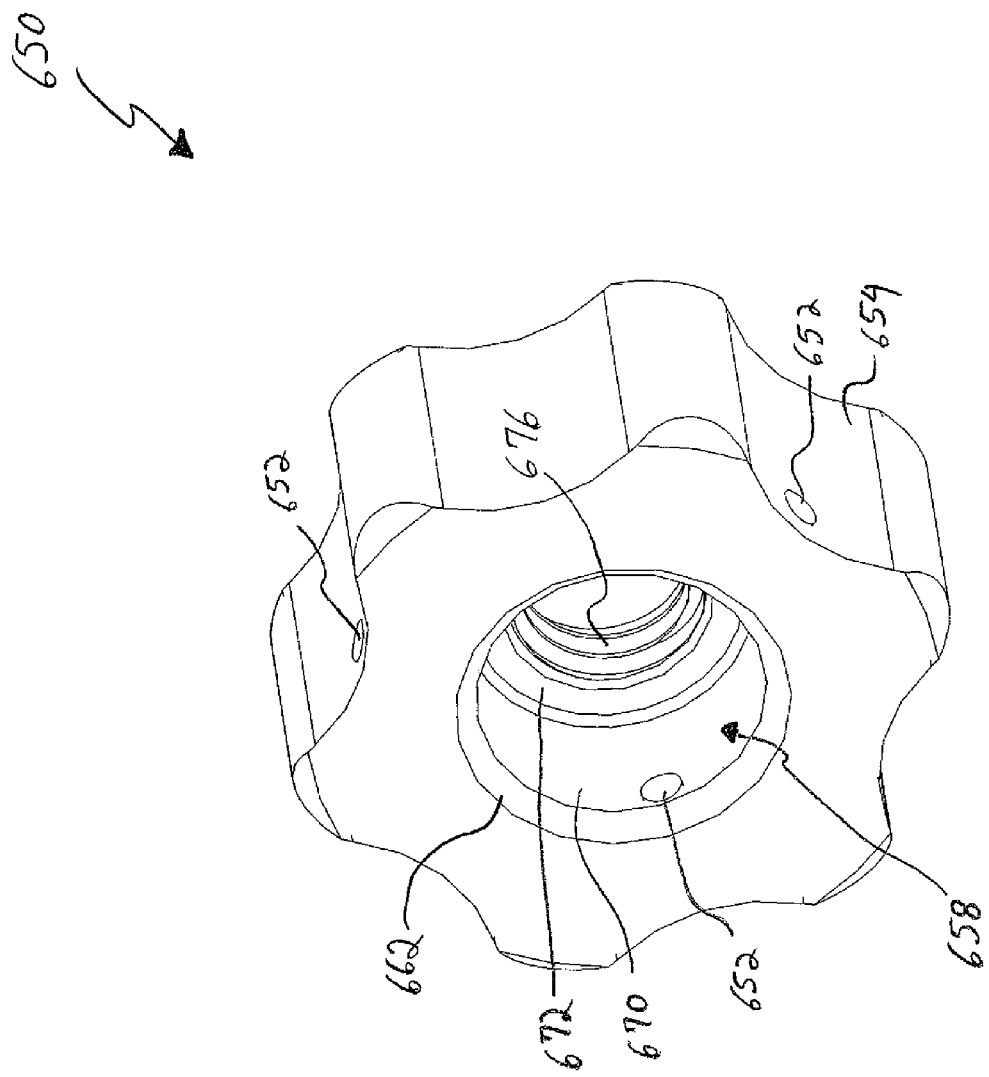
FIG. 27 is an elevated perspective view of the nut of FIG. 18.
Figure 28:
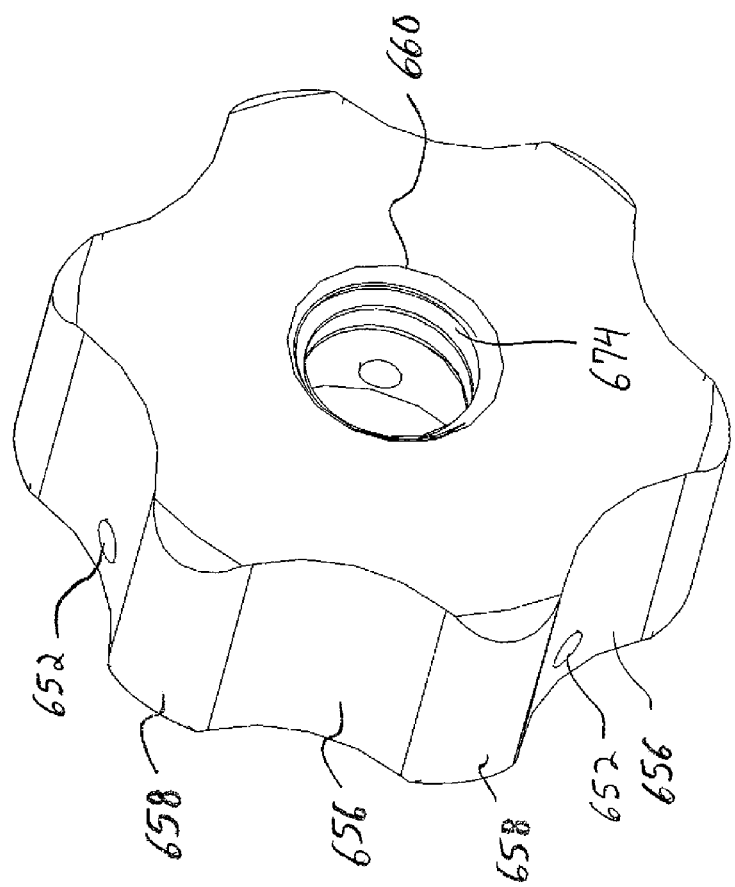
FIG. 28 is another elevated perspective view of the nut of FIG. 18.
Figure 29:
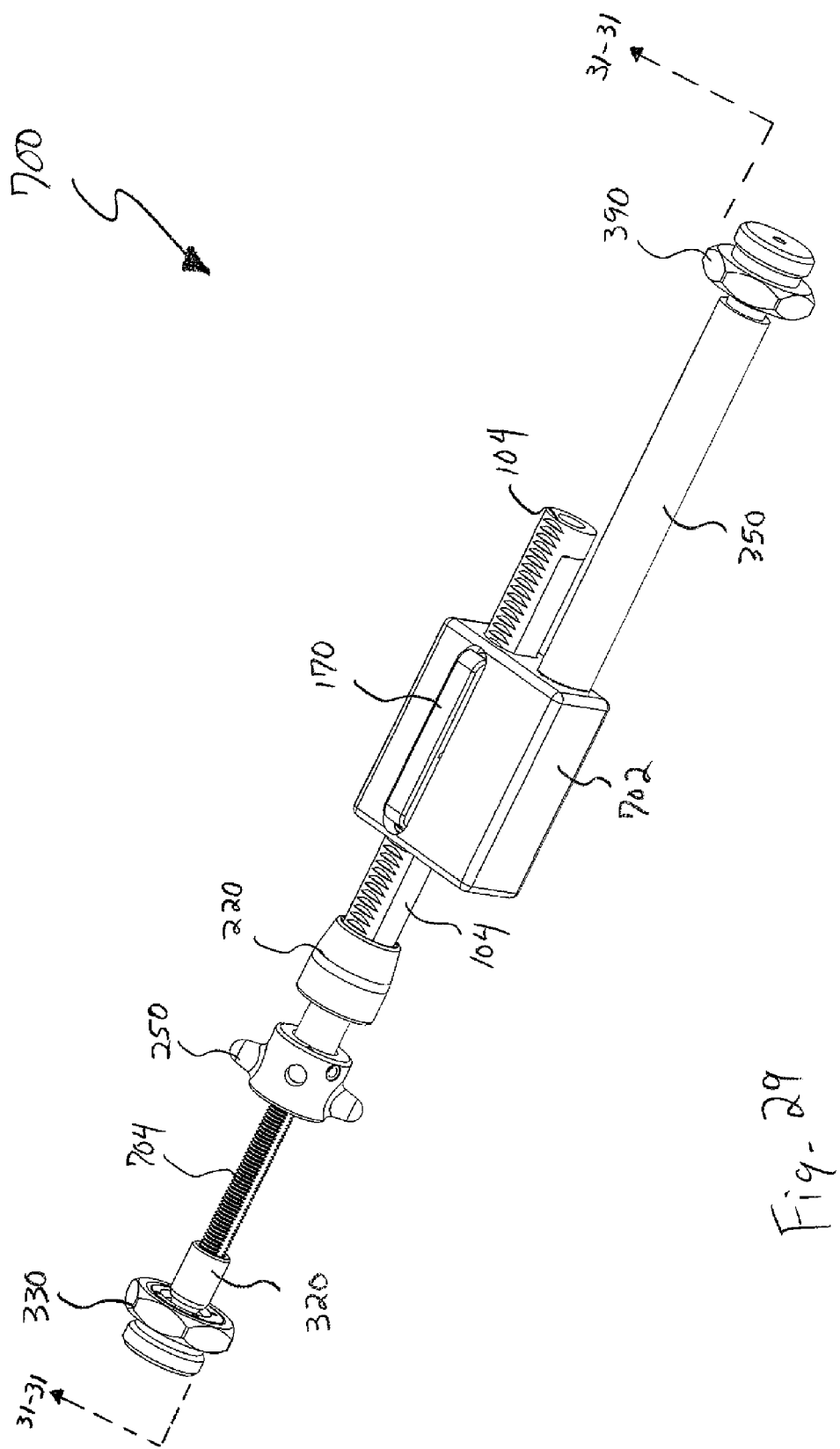
FIG. 29 is an elevated perspective view of an assembled third exemplary ratcheting strut in accordance with the instant disclosure.
Figure 30:
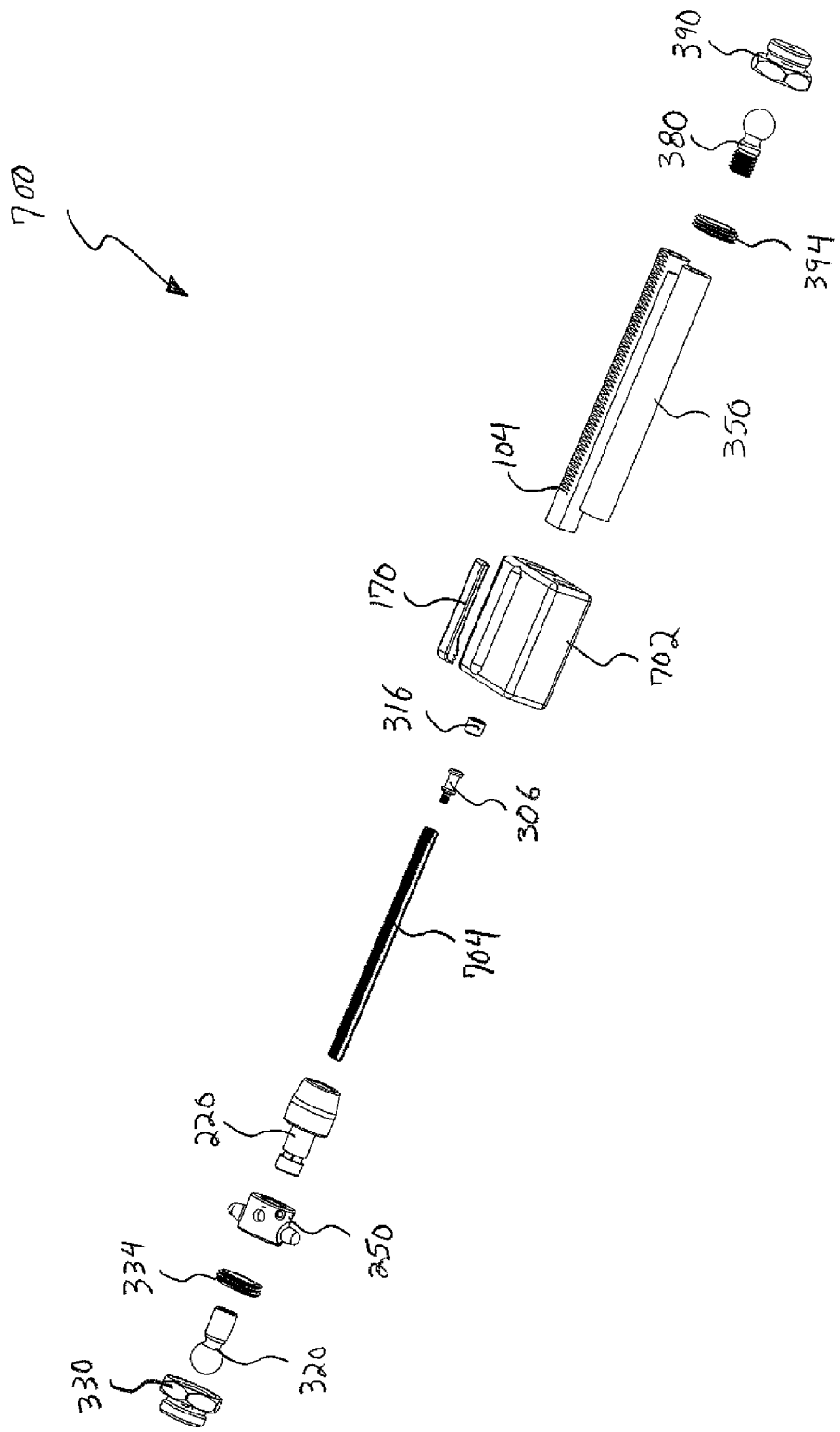
FIG. 30 is an exploded view of the third exemplary ratcheting strut of FIG. 29.
Figure 31:
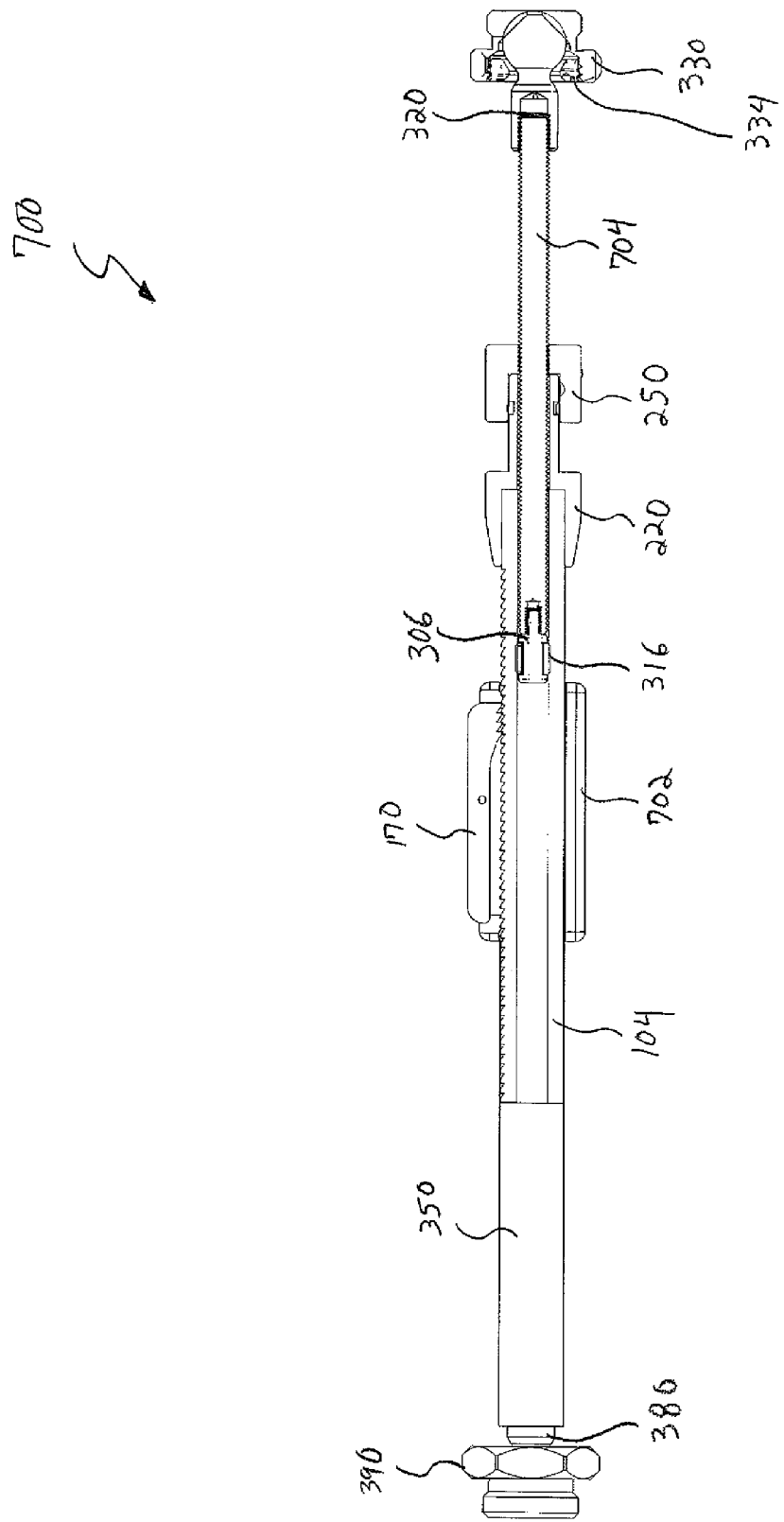
FIG. 31 is a cross-sectional view of the third exemplary ratcheting strut of FIG. 29 taken along line 31-31.
Figure 32:
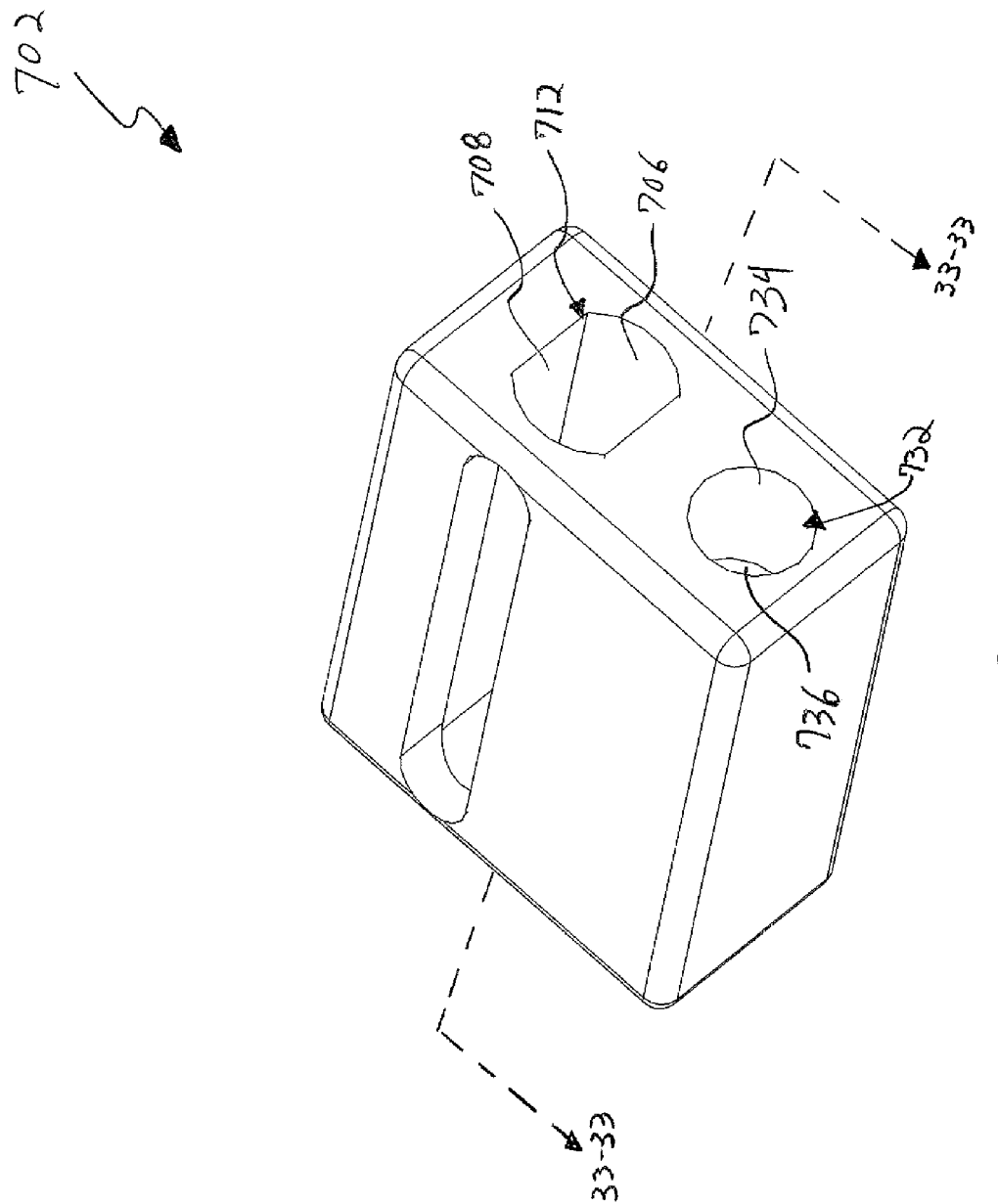
FIG. 32 is an elevated perspective view of the ratchet box of FIG. 29.
Figure 33:
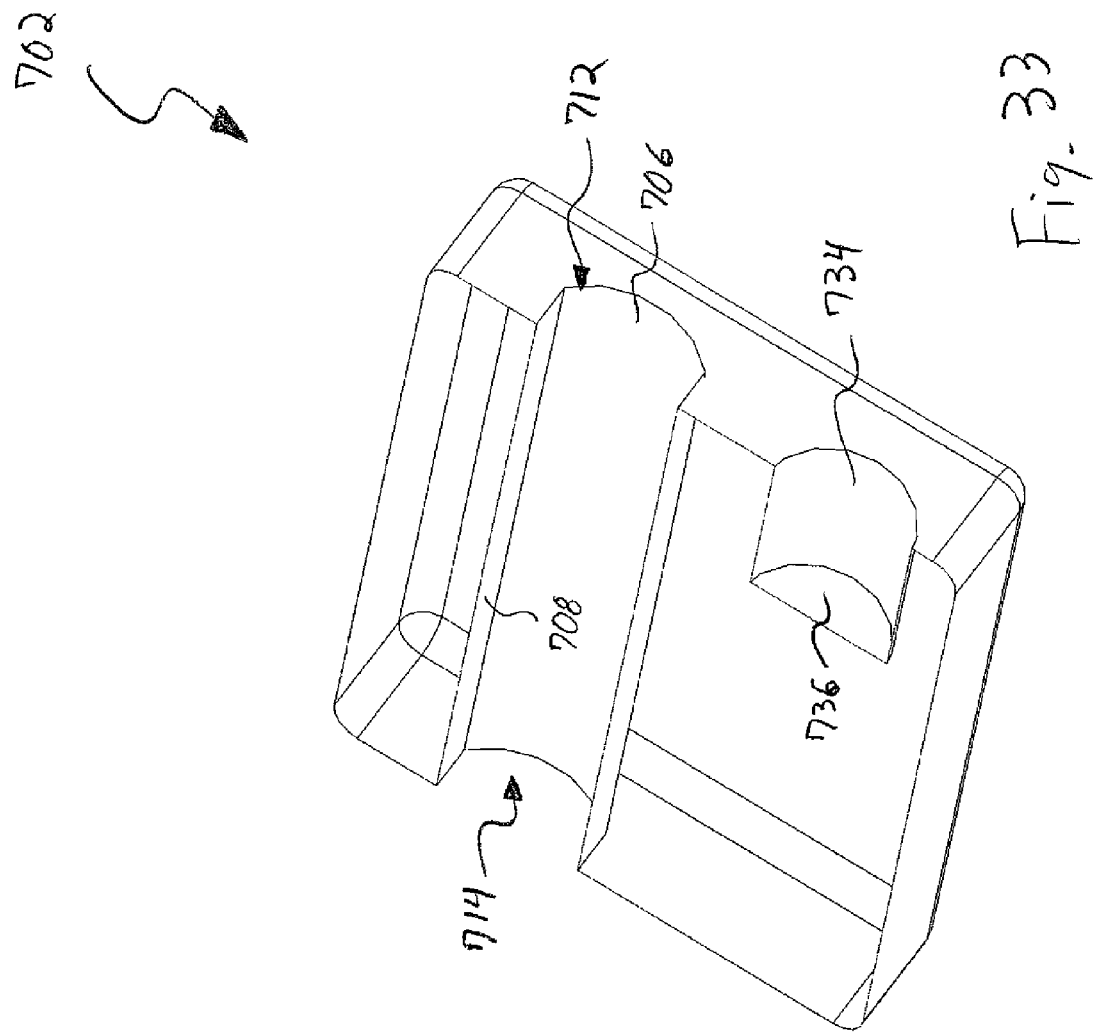
FIG. 33 is a cross-sectional view of the ratchet box of FIG. 32 taken along line 33-33.
Figure 34:
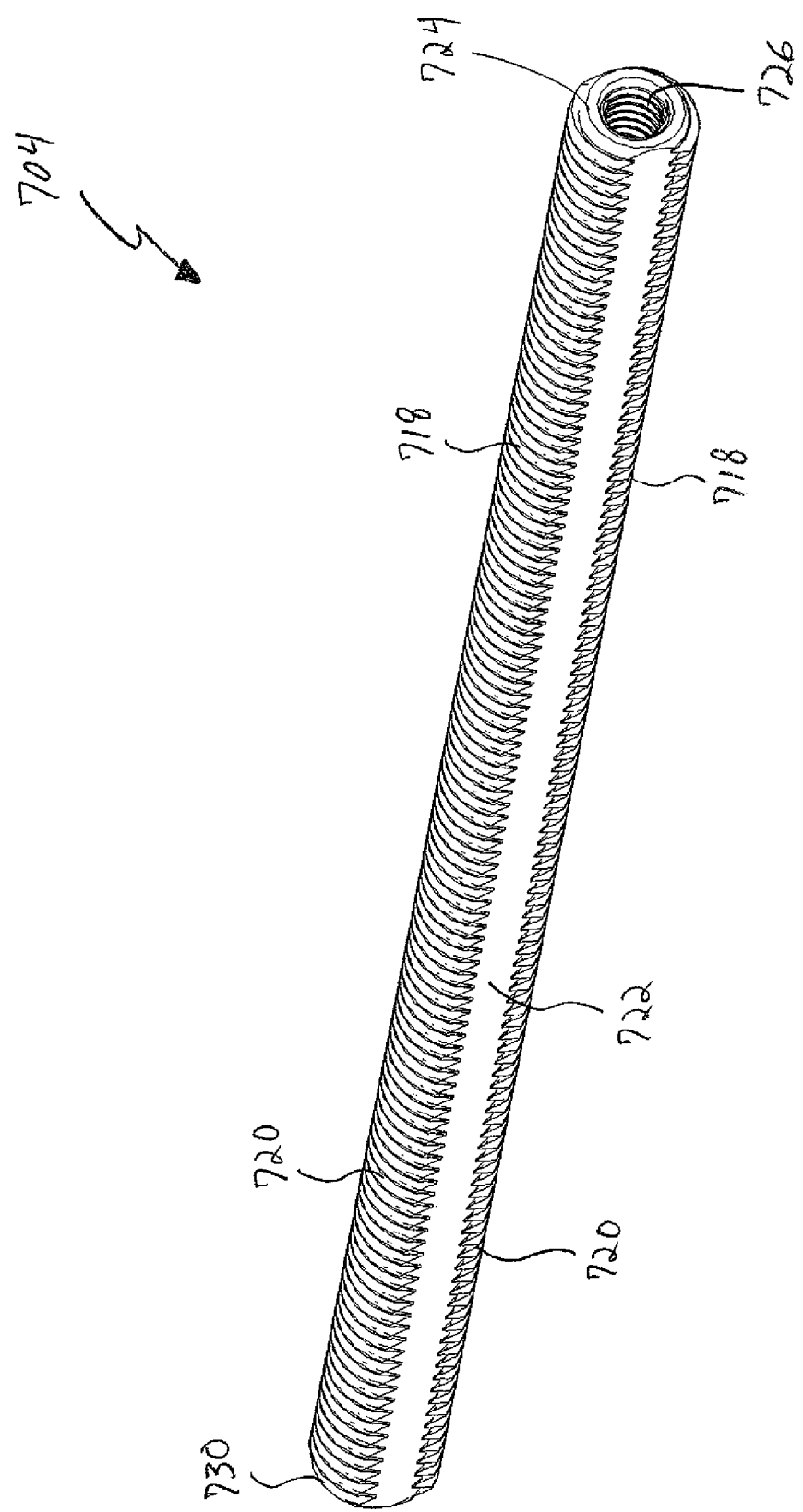
FIG. 34 is an elevated perspective view of the threaded post of FIG. 29.

As shown in FIG. 17, the ball joint cap 394 is ring-shaped and includes a central opening defined by an arcuate circumferential surface 404. This arcuate circumferential surface 404 cooperates with the semispherical depression of the ball joint housing 390 to create the spherical socket within which the spherical ball end 382 is able to rotate and pivot. In this exemplary embodiment, the diameter of the central opening of the ball joint cap 394 is less than the diameter of the spherical ball end 382 within the ball joint housing 390 so that once the ball joint cap and ball joint housing are mounted to one another with the spherical ball end 382 located therein, removal of the spherical ball end is not possible without discontinuing the ball joint cap from being mounted to ball joint housing.

Referencing FIGS. 18-28, a second exemplary ratcheting strut 500 makes use of several component parts of the first exemplary ratcheting strut 100. For example, the second ratcheting strut 500 uses the same tube mount 220, the threaded post 284, the post cap 306, the friction sleeve 316, the ball joint 320, the second tube 350, and the ball joint 380. Accordingly, a detailed description of these components has been omitted as part of discussing the second exemplary ratcheting strut 500 to omit redundancy, thereby furthering brevity.

This second exemplary ratcheting strut 500 includes a ratchet box 502 having a longitudinal opening extending therethrough that accommodates throughput of a ratchet tube 504. In exemplary form, the longitudinal opening is partially defined by a pair of arcuate interior walls 506 (partial cylindrical) circumferentially interposed a pair of planar walls 508. The planar walls 508 are parallel to one another and spaced apart from one another a first predetermined distance that is less than a distance (in effect, the diameter of a cylinder the arcuate walls would be a part of) the arcuate walls 506 are spaced apart from one another. In this fashion, the planar walls 508 operate to narrow the vertical cross-section in comparison to a hollow cylindrical cavity. Working together, the arcuate walls 506 and the planar walls 508 allow longitudinal traversal of the ratchet tube 504, while inhibiting axial rotation of the ratchet tube.

In this exemplary embodiment, the ratchet tube 504 comprises a cylindrical ring body having a cylindrical exterior surface 520 axially outset from a cylindrical interior surface 522. In this manner, the interior of the ratchet tube 504 is hollow and has a constant vertical, circular cross-section along its longitudinal length. An exterior surface of the ratchet tube 504 includes the cylindrical exterior surface 520, as well as a pair of planar surfaces 524 extending longitudinally along a majority of the longitudinal length of the ratchet tube. In exemplary form, these planar surfaces 524 may be formed by planarizing opposing sides of the ring body (i.e., hollow cylindrical tube) to remove material from the outside of the ring body, thereby decreasing the wall thickness of the ring body, but not impacting the dimensions of the cylindrical interior surface 522. In exemplary form, the material removed from the ring body can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. The planar surfaces 524, in exemplary form, do not extend along the entire longitudinal length of the ratchet tube 504 so that a distal end 526 of the ratchet tube is cylindrical, while the opposing proximal end 528 of the ratchet tube is partially cylindrical. More specifically, a pair of arcuate surfaces 532, 534 extends between the planar surfaces 524 to partially define the exterior of the ratchet tube. Each arcuate surface 532, 534 is separated from the other cylindrical surface by approximately ninety rotational degrees, except for the distal end where the arcuate surfaces seamlessly intersect with the cylindrical exterior surface 520. Both the dorsal and ventral arcuate surfaces 532 include a series of angled depressions 536 that are longitudinally repeated and consistently spaced apart from one another, thereby resulting in a series of angled teeth 538 that are longitudinally inset from the distal and proximal ends 526, 528 of the ratchet tube 504. In exemplary form, each tooth 538 includes a vertical surface 544 and an inclined surface 546 that intersects the vertical surface to form a horizontal peak 548. As will be discussed in more detail hereafter, the angled nature of the inclined surfaces 546 cooperate with corresponding surfaces of a pair of repositionable levers 570A, 570B to allow ratcheting action between the levers and the ratchet tube 504.

The shape of the ratchet tube 504 allows it to be inserted into the longitudinal opening of the ratchet box 502 so that the proximal end 528 of the ratchet tube is inserted into a distal opening 554 of the ratchet box 502 and extends through a proximal opening 556 prior to insertion of the distal end 526 into the interior of the ratchet box. The distal opening 554 is defined by a cylindrical interior wall 560 having a diameter larger than the arcuate interior walls 506. This cylindrical interior wall 560 extends proximally until terminating at a distal flange 562 that extends between the cylindrical interior wall and the arcuate interior walls 506. It should be noted that the cylindrical interior wall 560 and the arcuate interior walls 506 are coaxial with one another.

In this exemplary embodiment, the distal flange 560 is operative to inhibit throughput of objects having a cross-sectional distance larger than the distance between the planar walls 508. As mentioned previously, the distal end 526 of the ratchet tube 504 is cylindrical and exhibits a constant exterior diameter, whereas the proximal end 528 and a majority of the longitudinal length of the ratchet tube exhibits a cross-section that is partially circular with respect to the arcuate surfaces 532, 534, but is partially rectangular with respect to the planar surfaces 524. This dual shape (circular and rectangular) profile is also consistent with the dual shape profile on the interior walls 506, 508 of the ratchet box 102. In exemplary form, the exterior diameter (between the arcuate surfaces 532, 534) of the ratchet tube 504 is slightly less than the internal diameter of the arcuate interior walls 506. Likewise, the horizontal width between the planar surfaces 508 is slightly larger than the horizontal distance between the planar surfaces 524. As a result, the proximal end 528 of the ratchet tube 504 is able to be longitudinally repositioned along the entire length of the longitudinal opening of the ratchet box 502, whereas the distal end 526 of the ratchet tube is able to be longitudinally repositioned within only a portion of the longitudinal opening because the distal end cannot pass beyond the distal flange 562. In this manner, when the proximal end 528 of the ratchet tube 504 is first inserted into the distal opening 554 of the ratchet box 502 and longitudinally repositioned proximally, eventually the distal end 526 of the ratchet tube (where the planar surfaces 524 terminate and the uniform circumferential surface begins) abuts the distal flange 562, which prohibit further proximal motion of the ratchet tube.

In order to fix the position of the ratchet tube 504 with respect to the ratchet box 502, two levers 570A, 570B are repositionably mounted to the ratchet box to selectively engage the ratchet tube. More specifically, each lever 570A, 570B comprises an L-shaped beam 572 having a cylindrical pivot orifice 574 that accepts a dowel 576 concurrently seated within a respective cylindrical dowel orifice 578 in order to mount the ratchet box 502 to the lever. In exemplary form, each dowel 576 is cylindrical and has an external diameter that is slightly larger than the internal diameter of the corresponding cylindrical dowel orifice 578, thus securing the dowel in position via a friction fit. In contrast, the diameter of the corresponding cylindrical pivot orifice 574 is slightly larger than the external diameter of the respective dowel 576, thereby allowing pivoting motion of the lever 570A, 570B around the dowel.

In this exemplary embodiment, each lever 570A, 570B is biased by a spring 580 to engage the ratchet tube 504. More specifically, the coil spring 580 is seated within a respective spring receiver 582 of the ratchet box 502. Each spring receiver 582 comprises a ring-shaped depression that circumscribes a cylindrical projection that is adapted to be partially inserted into one end of the coil spring 580. Similarly, the underside of the lever 570S, 570B also includes a spring receiver 584 that likewise comprises a ring-shaped depression that circumscribes a cylindrical projection adapted to be partially inserted into the other end of the coil spring 580. The bias of the coil spring 580 is selected or set so that when no affirmative pressure is applied by a user to the lever 570A, 570B, a head 588 of the lever contacts the ratchet tube 504. In exemplary form, the head 588 of each lever 570A, 570B includes a series of angled teeth 592 that are each formed by the interaction of a vertical surface 594 and an inclined surface 596 that intersects the proximal surface to form a horizontal peak 598. In this fashion, the angled teeth 592 of each lever 570A, 570B are inclined to match the incline of the angled teeth 538 of the ratchet tube 504 nearest to each lever. As a result, when no affirmative pressure is applied by a user to the lever 570A, the ratchet tube 504 may not be repositioned proximally because the other lever 570B inhibits travel as the vertical surfaces 594 of the lever 570B teeth 592 contact the vertical surfaces 544 of the ratchet tube 504 lower teeth 538. Likewise, when no affirmative pressure is applied by a user to the lever 570B, the ratchet tube 504 may not be repositioned distally because the other lever 570A inhibits travel as the vertical surfaces 594 of the lever 570A teeth 592 contact the vertical surfaces 544 of the ratchet tube 504 upper teeth 538. As a result, in order to reposition the ratchet tube 504 proximally, a user needs to apply an affirmative pressure to the lever 570B to overcome the spring bias of the spring 580 and vertically separate the vertical surfaces 594 of the lever 570B teeth 592 with the vertical surfaces 544 of the ratchet tube 504 lower teeth 538. It does not matter that the other lever 570A continues to engage the ratchet tube 504 because the inclined surfaces 596 of the teeth 592 of the other lever 570A are engaging the inclined surfaces 546 of the upper teeth 538, thereby allowing the inclined surfaces 546, 596 to slide against one another so that the ratchet tube 504 may be repositioned proximally. When the appropriate proximal travel is reached, the user simply discontinues affirmative pressure to the lever 570B, thereby allowing the spring 580 bias to dominate and cause the lever 570B to contact the ratchet tube 504 so that the vertical surfaces 144, 194 contact one another and do not allow proximal motion. Conversely, in order to reposition the ratchet tube 504 distally, a user needs to apply an affirmative pressure to the lever 570A to overcome the spring bias of the spring 580 and vertically separate the vertical surfaces 594 of the lever 570A teeth 592 with the vertical surfaces 544 of the ratchet tube 504 upper teeth 538. It does not matter that the other lever 570B continues to engage the ratchet tube 504 because the inclined surfaces 596 of the teeth 592 of the other lever 570B are engaging the inclined surfaces 546 of the lower teeth 538, thereby allowing the inclined surfaces 546, 596 to slide against one another so that the ratchet tube 504 may be repositioned distally. When the appropriate distal travel is reached, the user simply discontinues affirmative pressure to the lever 570A, thereby allowing the spring 580 bias to dominate and cause the lever 570A to contact the ratchet tube 504 so that the vertical surfaces 144, 194 contact one another and do not allow distal motion.

Each lever 570A, 570B may also be locked in position so that the teeth 592 engage the angled teeth 538 of the ratchet tube 504. In order to lock either lever 570A, 570B in an engaged position with the ratchet tube 504, the lever includes a lock orifice 600 that is sized to receive a portion of a thumb screw 204. The thumb screw 204 includes a knob 206 mounted to a perpendicularly extending, linear projection 208 having threads 210 adapted to engage threads (not shown) on the inside of a thumb screw orifice 614 extending through the ratchet box 102. When the projection 208 of the thumb screw 204 is inserted through the thumb screw orifice 614 and lock orifice 600 for a respective lever, the lever 570A, 570B is not pivotally repositionable so that the teeth 592 of the lever are out of the line of travel of the teeth 538 of the ratchet tube 504. Consequently, to pivot either lever 570A, 570B so that the teeth 592 of the lever are out of the line of travel of the teeth 538 of the ratchet tube 504, the thumb screw 204 needs to be positioned so that the projection 208 is no longer received within the lock orifice 600. After the thumb screw 204 is positioned so that the projection 208 is no longer received within the lock orifice 600, the lever 570A, 570B may be repositioned by application of affirmative pressure to overcome the bias of the spring 580, thereby pivoting the lever so that the teeth 592 of the lever are out of the line of travel of the teeth 538 of the ratchet tube 504.

When the ratchet tube 504 is repositioned with respect to the ratchet box 502, other components mounted to the ratchet tube are also repositioned. In this exemplary embodiment, a tube mount 220 is coupled to the proximal end 528 of the ratchet tube via a friction fit. A nut 650 is mounted to the tube mount 220 and is rotationally repositionable with respect thereto. The nut 650 includes one or more through set screw orifices 652 that extend from an exterior surface 654 into a hollow interior 658, which includes proximal and distal openings 660, 662. The exterior surface 654 comprises a hexagonal pattern of six alternating arcuate troughs 656 and six arcuate projections 658 that provide grip for a user to grasp the nut 650 and facilitate rotation of the nut with respect to the sleeve 236 of the tube mount 220. In this exemplary embodiment, the distal opening 662 allows access to a cylindrical cavity defined by a circumferential interior wall 670. At the proximal end of this interior wall 678 is a flange 672 that provides an abutment surface against which the exposed proximal end of the sleeve 236 contacts when fully seated within the nut 650. The flange 672 also operates to decrease the diameter of the hollow interior 658 and abuts a cylindrical interior surface 674 having threads 676 adapted to be engaged by the threads 298 of the threaded post 284 that extends through the nut 650, the tube mount 220, and partially through an interior of the ratchet tube 504. It is these partial threads 298 that are adapted to engage the threads 676 of the nut 650 so that rotational repositioning of the nut results in longitudinal repositioning of the threaded post 284. More specifically, clockwise rotation of the nut 650 may reposition the threaded post 284 longitudinally in a distal direction, while clockwise rotation of the nut 650 may reposition the threaded post 284 longitudinally in a proximal direction, or vice versa.

As with the first exemplary ratcheting strut 100, this second exemplary ratcheting strut 500 includes a ball joint 320 mounted to the threaded post 284. Similarly, this second exemplary ratcheting strut 500 also includes a second tube 350 mounted to the ratchet box 502 and a ball joint 380 mounted to the second tube. For purposes of illustration only with respect to this second exemplary ratcheting strut 500, the ball joint housing and ball joint cap for each ball joint 320, 380 have been omitted. Nevertheless, it is to be understood that the second exemplary ratcheting strut 500 includes a ball joint housing and a ball joint cap for each ball joint 320, 380.

Referencing FIGS. 29-34, a third exemplary ratcheting strut 700 makes use of several component parts of the first exemplary ratcheting strut 100. For example, the third ratcheting strut 700 uses the same ratchet tube 104, repositionable lever 170, tube mount 220, nut 250, post cap 306, friction sleeve 316, ball joint 320, ball joint housings 330, 390, ball joint caps 334, 394, second tube 350, and ball joint 380. Accordingly, a detailed description of these components has been omitted as part of discussing the third exemplary ratcheting strut 700 to omit redundancy, thereby furthering brevity. Essentially, the third exemplary ratcheting strut 700 differs from the first exemplary ratcheting strut 100 by the ratchet box 702 and threaded post 704.

This third exemplary ratcheting strut 700 includes a ratchet box 702 having a longitudinal opening extending therethrough that accommodates throughput of a ratchet tube 104. In exemplary form, the longitudinal opening is partially defined by a pair of arcuate interior walls 706 (partial cylindrical) circumferentially interposed a pair of planar walls 708. The planar walls 708 are parallel to one another and spaced apart from one another a first predetermined distance that is less than a distance (in effect, the diameter of a cylinder the arcuate walls would be a part of) the arcuate walls 706 are spaced apart from one another. In this fashion, the planar walls 708 operate to narrow the vertical cross-section in comparison to a hollow cylindrical cavity. Working together, the arcuate walls 706 and the planar walls 708 allow longitudinal traversal of the ratchet tube 104, while inhibiting axial rotation of the ratchet tube.

The shape of the ratchet tube 104 allows it to be inserted into the longitudinal opening of the ratchet box 702 so that the proximal end 128 of the ratchet tube is inserted into a distal opening 712 of the ratchet box 702 and extends through aproximal opening 714 prior to insertion of the distal end 126 into the interior of the ratchet box.

In this exemplary embodiment, the dimensions of the distal and proximal openings 712, 714 are operative to inhibit complete throughput of objects having a cross-sectional distance larger than the distance between the planar walls 708. Because the distal end 126 of the ratchet tube 104 is cylindrical and exhibits a constant exterior diameter, whereas the proximal end 128 and a majority of the longitudinal length of the ratchet tube exhibits a cross-section that is partially circular with respect to the arcuate surfaces 132, 134, but is partially rectangular with respect to the planar surfaces 124. This dual shape (circular and rectangular) profile is also consistent with the dual shape profile on the interior walls 706, 708 of the ratchet box 702. In exemplary form, the exterior diameter (between the arcuate surfaces 132, 134) of the ratchet tube 104 is slightly less than the internal diameter of the arcuate interior walls 706. Likewise, the horizontal width between the planar surfaces 708 is slightly larger than the horizontal distance between the planar surfaces 124. As a result, the proximal end 128 of the ratchet tube 104 is able to be longitudinally repositioned along the entire length of the longitudinal opening of the ratchet box 702, whereas the distal end 126 of the ratchet tube is able to be longitudinally repositioned within only a portion of the longitudinal opening because the distal end cannot pass into the interior of the ratchet box. In this manner, when the proximal end 128 of the ratchet tube 104 is first inserted into the distal opening 712 of the ratchet box 702 and longitudinally repositioned proximally, eventually the distal end 126 of the ratchet tube (where the planar surfaces 124 terminate and the uniform circumferential surface begins) abuts the outside of the ratchet box, which prohibits further proximal motion of the ratchet tube.

In order to fix the position of the ratchet tube 104 with respect to the ratchet box 702, a lever 170 is repositionably mounted to the ratchet box to selectively engage the ratchet tube. Reference is had to the previous discussion of how the ratchet tube 104 and 170 interact to allow or retard repositioning of the ratchet tube.

When the ratchet tube 104 is repositioned with respect to the ratchet box 702, other components mounted to the ratchet tube are also repositioned. In this exemplary embodiment, a tube mount 220 is coupled to the proximal end 128 of the ratchet tube via a friction fit. A nut 250 is mounted to the tube mount 220 and is rotationally repositionable with respect thereto. The nut 250 includes threads 276 that engage threads 718 of the threaded post 704 while the threaded post extends through the nut, the tube mount 220, and partially through an interior of the ratchet tube 104. It is these threads 718 that are adapted to engage the threads 276 of the nut 250 so that rotational repositioning of the nut results in longitudinal repositioning of the threaded post 704.

In exemplary form, the threaded post 704 comprises a hybrid exterior surface comprising a pair of arcuate surfaces 720 that are interposed by a pair of planar surfaces 722 extending longitudinally along the longitudinal length of the threaded post. In exemplary form, these planar surfaces 722 may be formed by planarizing opposing sides of a cylinder to remove material from the exterior, thereby decreasing the thickness of the cylinder at certain circumferential locations. In exemplary form, the material removed from the cylinder can be cross-sectionally represented as a first area outlined by a first chord extending between circumferential exterior points at zero degrees and ninety degrees and by the circumferential surface extending between the same points at zero degrees and ninety degrees. Similarly, the second area may be outlined by a second chord extending between one hundred eighty degrees and two hundred seventy degrees and by the circumferential surface extending between the same points at one hundred eighty degrees and two hundred seventy degrees. Both arcuate surfaces 720 are tapped to provide a series of repeating threads 718. It is these threads 718 that are adapted to engage the tapped surfaces 276 of the nut 250 so that rotational repositioning of the nut results in longitudinal repositioning of the threaded post 704. More specifically, clockwise rotation of the nut 250 may reposition the threaded post 704 longitudinally in a distal direction, while clockwise rotation of the nut 250 may reposition the threaded post 704 longitudinally in a proximal direction, or vice versa.

A distal end 724 of the threaded post 704 includes a cylindrical cavity that is tapped to provide internal threads 726. These threads 726 are adapted to be engaged by the threads 304 of the post cap 306, which is mounted to the friction sleeve 316. As discussed previously, the diameter of the cylindrical interior surface 122 of the ratchet tube 104 is slightly less than the exterior diameter of the friction sleeve 316, thereby allowing the post cap and friction sleeve to slide longitudinally within the interior of the ratchet tube, but with a predetermined resistance. But this frictional resistance is not so great as to inhibit longitudinal motion of the sleeve 316, the post cap 306, and threaded post 704 when the nut 250 is rotated.

A proximal end 730 of the threaded post 704 is mounted to a ball joint 320 having a spherical ball end 322 integrally formed with a hollow cylinder 324. The hollow cylinder is threaded and these threads 328 are adapted to engage the threads 718 of the threaded post 704 in order to mount the threaded post to the ball joint 320 via a friction fit. Similar to the first exemplary ratcheting strut 100, this third ratcheting strut also includes a ball joint housing 330 and a ball joint cap 334.

Referring back to FIGS. 32 and 33, the ratchet box 702 includes a cylindrical cavity 732 that extends in parallel to, but is offset from, the longitudinal opening. This cylindrical cavity is adapted to receive a portion of the second tube 250 and is bounded by a cylindrical interior wall 734 that abuts a circular, planar wall 736. In exemplary form, the diameter of the cylindrical interior wall 734 is slightly less than the exterior diameter of the second tube 250, thereby mounting the ratchet box 702 to the second tube once an end of the second tube is inserted deep enough to abut the planar wall.

As with the first exemplary ratcheting strut 100, the second tube 250 of the third exemplary ratcheting strut 700 is mounted to a ball joint 380 that includes a male connection comprising an external circumferential surface 374 threaded to fit within and engage the threaded circumferential surface 370 of the smaller diameter cylindrical cavity of the second tube 350. Likewise, this third ratcheting strut 700 also includes a ball joint housing 330 and a ball joint cap 334.

Unlike the previous two exemplary ratcheting struts 100, 500 that included ratcheting structures that were coaxial with the second tube 350, this third exemplary ratcheting strut 700 has the ratcheting structures axially offset, but in parallel with, the second tube. This offset orientation has the advantages of allowing more adjustable length, allowing use of solid bodies, easier manufacture, and increased strength.

Following from the above description and invention summaries, it should be apparent to those of ordinary skill in the art that, while the methods and apparatuses herein described constitute exemplary embodiments of the present invention, the invention is not limited to the foregoing and changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of adjusting a fracture fixation device, the method comprising:
   providing a ratcheting strut including a ratchet box, a first tube sized to extend at least partially into a passage of the ratchet box, the first tube including a first portion having a substantially cylindrical exterior surface and second portion having first and second planar surfaces substantially parallel to one another and defined along the first tube, such that the first portion is configured to restrict longitudinal movement of the first tube, and a second tube mounted to the ratchet box in a co-axial manner to the first tube, the first tube being repositionable with respect to the second tube in predetermined increments along a longitudinal axis;
   actuating a lever of the ratchet box to cause a first set of teeth on the first tube to disengage from a second set of teeth on the lever;
   moving the first tube from a first position to a second position along the longitudinal axis as the lever is actuated; and
   releasing the lever to cause the first set of teeth to reengage the second set of teeth once the first tube is in the second position.

2. The method of claim 1, wherein the step of actuating the lever of the ratchet box comprises pivoting the lever about a dowel from a first position to a second position.

3. The method of claim 2, wherein the step of pivoting the lever about the dowel comprises overcoming a spring that is configured to bias the second set of teeth into engagement with the first set of teeth.

4. The method of claim 1, further comprising the step of incrementally repositioning an extension post operably coupled to the first tube along the longitudinal axis, the extension post being configured to at least partially extend into an opening of the first tube.

5. The method of claim 4, wherein the step of incrementally repositioning the extension post comprises rotating a nut associated with the extension post.

6. The method of claim 1, further comprising the step of locking the engagement of the first set of teeth to the second set of teeth by adjusting a knob mounted to the ratchet box.

7. The method of claim 6, wherein the step of adjusting the knob comprises threading a screw to a lock orifice of the lever.

* * * * *

UNITED STATES PATENT AND TRADEMARK OFFICE
CERTIFICATE OF CORRECTION

| | | |
|---|---|---|
| PATENT NO. | : 9,474,552 B2 | Page 1 of 1 |
| APPLICATION NO. | : 13/464502 | |
| DATED | : October 25, 2016 | |
| INVENTOR(S) | : Barnett et al. | |

It is certified that error appears in the above-identified patent and that said Letters Patent is hereby corrected as shown below:

On the Title Page

In item (75), in "Inventors", in Column 1, Line 4, delete "Philip" and insert --Phillip--, therefor Signed and Sealed this
Eighth Day of May, 2018

Andrei Iancu
*Director of the United States Patent and Trademark Office*